United States Patent [19]

Yayon et al.

[11] Patent Number: 5,270,197
[45] Date of Patent: Dec. 14, 1993

[54] CELLS EXPRESSING A SUBSTANTIAL NUMBER OF SURFACE HIGH AFFINITY HBGF RECEPTORS BUT RELATIVELY FEW LOW AFFINITY HBGF BINDING SITES AND SYSTEM FOR ASSAYING BINDING TO HBGF RECEPTOR

[75] Inventors: Avner Yayon, Rehovot, Israel; David M. Ornitz, Brookline, Mass.; Michael Klagsbrun, Newton, Mass.; Philip Leder, Chestnut Hill, Mass.

[73] Assignees: The Children's Medical Center Corp., Boston; President and Fellows of Harvard College, Cambridge, both of Mass.

[21] Appl. No.: 631,717

[22] Filed: Dec. 20, 1990

[51] Int. Cl.$^5$ .................. C12N 5/10; C12N 15/85; C12P 21/00; G01N 33/566
[52] U.S. Cl. .................. 435/240.2; 435/69.1; 435/172.3; 435/7.21
[58] Field of Search .................. 435/69.1, 172.3, 240.2, 435/7.21

[56] References Cited

U.S. PATENT DOCUMENTS 4,882,275 11/1989 Klagsburn .................. 435/68

OTHER PUBLICATIONS

Yayon et al., "Cell Surface, Heparin-like Molecules Are Required for Binding . . . ", *Cell* 64:841-848, Feb. 22, 1991.
Dionne et al., Cloning and expression of two distinct high-affinity receptors . . . , *The EMBO Journal* 9:2685-2692, Sep. 1990.
Azizkhan et al.; Mast Cell Heparin Stimulates Migration of Capillary Endothelial Cells In Vitro; *J. Exp. Med.;* 152:931-44; Oct. 1980.
Mansukhani et al.; A murine fibroblast growth factor (FGF) receptor expressed in CHO cells is activated by basic FGF and Kaposi FGF; *Proc. Natl. Acad. Sci.;* 87:4378-82; Jun. 1990.
Pasquale et al.; Identification of a developmentally regulated protein-tyrosine kinase by using anti-phosphotyrosine antibodies to screen a cDNA expression library; *Proc. Natl. Acad. Sci.;* 86:5449-53; Jul. 1989.
Ruta et al.; A novel protein tyrosine kinase gene whose expression is modulated during endothelial cell differentiation; *Oncogene;* 3:9-15; 1988.
Safran et al.; The murine flg gene encodes a receptor for fibroblast growth factor; *Oncogene;* 5:635-43; 1990.
Shing et al.; Heparin Affinity: Purification of a Tumor-Derived Capillary Endothelial Cell Growth Factor; *Science;* 223:1296-99; Mar. 1984.
Baird et al.; Receptor- and heparin-binding domains of basic fibroblast growth factor; *Proc. Natl. Acad. Sci.* 85:2324-28; Apr. 1988.
Bashkin et al.; Basic Fibroblast Growth Factor Binds to a Subendothelial Extracellular Matrix and Is Released by Heparitinase and Heparin-like Molecules; *Biochem.;* 28:1737-43; 1989.
Dietrich et al.; Cell Recognition and Adhesivesness: A Possible Biological Role For The Sulfated Mucopolysaccharides; *Biochem. and Biophy. Resear. and Comm.;* 75:329-336; 1977.
Esko et al.; Tumor Formation Dependent on Proteoglycan Biosynthesis; *Science;* 241:1092-96; Aug. 1988.
Folkman et al., A Heparin-Binding Angiogenic Protein—Basic Fibroblast Growth Factor—Is Stored Within Basement Membrane; *Am. Jour. of Path.;* 130:393-400; Feb. 1988.
Folkman et al., Angiogenic Factors; *Science;* 235:442-447; Jan. 1987.

(List continued on next page.)

Primary Examiner—Robert A. Wax
Assistant Examiner—Stephen Walsh
Attorney, Agent, or Firm—Fish & Richardson

[57] ABSTRACT

A homogeneous population of cells having on average (1) a number of cell surface low-affinity heparin-binding growth factor (HBGF) sites per cell less than 20% of the number of such binding sites found on wild-type CHO-K1 cells (ATCC Accession No. CCL61), and at least three times the number of cell surface high-affinity HBGF receptors per cell found on such CHO-K1 cells; and an assay system utilizing such cells.

9 Claims, 24 Drawing Sheets

OTHER PUBLICATIONS

Gordon et al.; Extracellular Matrix Heparan Sulfate Proteoglycans Modulate the Mitogenic Capacity of Acidic Fibroblast Growth Factor; *Jour. of Cell. Phys.;* 140:584-92; 1989.

Gospodarowicz et al.; Heparin Protects Basic and Acidic FGF From Inactivation; *Jour. of Cell. Phys.;* 128:475-84; 1986.

Kaner et al.; Fibroblast Growth Factor Receptor Is a Portal of Cellular Entry for Herpes Simplex Virus Type 1 *Science;* 248:1410-13; Jun. 1990.

Klagsburn; The Fibroblast Growth Factor Family: Structural and Biological Properties; *Progress in Growth Factor Research;* 1:207-35; 1989.

Klagsbrun et al.; Heparin affinity of anionic and cationic capillary endothelial cell growth factors: Analysis of hypothalamus-derived growth factors and fibroblast growth factor; *Proc. Natl. Acad.;* 82:805-9; 1985.

Kornbluth et al.; Novel Tyrosine Identified by Phosphotyrosin Antibody Screening of cDNA Libraries; *Mole. and Cell. Biol.;* 8:5541-44; Dec. 1988.

Lee et al.; Purification and Complementary DNA Cloning of a Receptor for Basic Fibroblast Growth Factor; *Science;* 245:57-60; Jul. 1989.

Moscatelli; High and Low Affinity Binding Sites for bFGF on Cultured Cells: Absence of a Role for Low Affinity Binding in the Stim. of Plasminogen Activator Prod. by BCE Cells; *Jour. of Cell. Phys.;* 131:123-30; 1987.

Moscatelli; Metabolism of Receptor-bound and Matrix-bound Basic Fibroblast Growth Factor by Bovine Capillary Endothelial Cells; *Jour. of Cell. Biol;* 107:753-59; 1988.

Mueller et al.; Stabilization by Heparin of Acidic Fibroblast Growth Factor Mitogenicity for Human Endothelial Cells In Vitro; *Jour. of Cell. Phys.;* 140:439-48; 1989.

Neufeld et al.; Basic and Acidic Fibroblast Growth Factors Interact with the Same Cell Surface Receptors; *Jour. of Biol. Chem.;* 261:5631-37; 1986.

Rifkin et al.; Recent Developments in the Cell Biology of Basic Fibroblast Growth Factor; *Jour. of Cell. Biol.;* 109:1-6; Jul. 1989.

Sakseta et al.; Endothelial Cell-derived Heparan Sulfate Binds Basic Fibroblast Growth Factor and Protects it From Proteolytic Degradation; *Jour. of Cell. Biol.;* 107:743-51; Aug. 1988.

Seno et al.; Carboxyl-terminal structure of basic fibroblast growth factor significantly contributes to its affinity for heparin; *Eur. J. Biochem.;* 188:239-45; 1990.

Taylor et al.; Protamine is an inhibitor of angiogenesis; *Nature;* 297:307-12; May 1982.

Thornton et al.; Human Endothelial Cells: Use of Heparin in Cloning and Long-Term Serial Cultivation; *Science* pp. 623-625; Nov. 1983.

Vlodavsky et al.; Endothelial cell-derived basic fibroblast growth factor: Synthesis and deposition into subendothelial extracellular matrix; *Proc. Natl. Acad. Sci.;* 84:2292-96; Apr. 1987.

WuDunn et al.; Initial Interaction of Herpes Simplex Virus with Cells Is Binding to Heparin Sulfate; *Jour. of Virology;* 63:52-58; Jan. 1989.

```
  1  MWGWKCLLFW  AVLVTATLCT  ARPAPTLPEQ  AQPWGVPVEV  ESLLVHPGDL
 51  LQLRCRLRDD  VQSINWLXDG  VQLVESNRTR  ITGEEVEVRD  SIPADSGLYA
101  CVTSSPSGSD  TTYFSVNVSD  ALPSSEDDDD  DDDSSSEEKE  TDNTKPNPVA
151  PYWTSPEKME  KKLHRVPAAK  TVKFKCPSSG  TPNPTLRWLK  NGKEFKPDHR
201  IGGYKVRYAT  WSIIMDSVVP  SDKGNYTCIV  ENEYGSINHT  YQLDVVERSP
251  HRPILQAGLX  ANKTVALGSN  VEFMCKVYSD  PXPHIQWLKH  IEVNGSKIGP
301  DNLPYVQILK  TAGVNTTDKE  MEVLHLRNVS  FEDAGEYTCL  AGNSIGLSHH
351  SAWLTVLEAL  EERPAVMTSP  LYLEIIIYCT  GAFLISCMLG  SVIIYKMKSG
401  TKKSDFHSQM  AVHKLAKSIP  LRRQVTVSAD  SSASMNSGVL  LVRPSRLSSS
451  GTPMLAGVSE  YELPEDPRWE  LPRDRLVLGK  PLGEGCFGQV  VLAEAIGLDK
501  DKPNRVTKVA  VKMLKSDATE  KDLSDLISEM  EMMKMIGKHK  NIINLLGACT
551  QDGPLYVIVE  YASKGNLREY  LQARRPPGLE  YCYNPSHNPE  EQLSSKDLVS
601  CAYQVARGME  YLASKKCIHR  DLAARNVLVT  EDNVMKIADF  GLARDIHHID
651  YYKKTTNGRL  PVKWMAPEAL  FDRIYTHQSD  VWSFGVLLWE  IFTLGGSPYP
701  GXPVEELFKL  LKEGHRMDKP  SNCTNELYMM  MRDCWHAVPS  QRPTFKQLVE
751  DLDRIVALTS  NQEYLDLSIP  LDQYSPSFPD  TRSSTCSSGE  DSVFSHEPLP
801  EEPCLPRHPT  QLANSGLKRR  *
```

FIG. 9A

```
              E
E             H          Ac    H
c             AaSX       BhoNBa            G
o             vemm       aa7abe            s
R             alaa       nI8reI            u
I             IIII       IIIIII            I
             /  /             / /
    GGAATTCGGCACGAGCGCCCGGGCTGGAGGCGCCCGGCTCGGAGTGCCGCCGGGAGTCGT
1   ----------+----------+----------+----------+----------+----------+ 60
    CCTTAAGCCGTGCTCGCGGGCCCGACCTCCGCGGGCCGAGCCTCACGGCGGCCCTCAGCA

N  S  A  R  A  P  G  L  E  A  P  G  S  E  C  R  R  E  S  C -

B                              B
                           s                              s
         X  N      E       p                              p
         Gm sS     c   B   l                              Bl
         CdaD pa   o   aA2SX            X    A            a2
         fIIs Bc   3   nv8ch            h    l            n8
         rIIa II   1   Ia6io            o    w            I6
         IIII II   I   IIIII            I    N            II
                           I                              I
        //              / /                                /
    GCCTCGGCCGCGGAGCCCTCGAGACCCCATCAGGATCTGAACGGAGCCCGGAGACGAGCG
61  ----------+----------+----------+----------+----------+----------+ 120
    CGGAGCCGGCGCCTCGGGAGCTCTGGGGTAGTCCTAGACTTGCCTCGGGCCTCTGCTCGC

L  G  R  G  A  L  E  T  P  S  G  S  E  R  S  P  E  T  S  G -

G  D
                              s  s
                              u  a
                              I  I
    GCGGGAcGCAAGACACAGACACCCSCCSCGCCACGgACAGCTCTCCAGAGGCGGGACCGC
121 ----------+----------+----------+----------+----------+----------+ 180
    CGCCCTgCGTTCTGTGTCTGTGGGSGGSGCGGTGCcTGTCGAGAGGTCTCCGCCCTGGCG

G  T  Q  D  T  D  T  ?  ?  A  T  D  S  S  P  E  A  G  P  O -

H                                           DNS
             a                                           sct
             e                                           aoy
             I                                           III
             I                                            //
    AGCGCCAAGTGAGAGTCAGCTTGCGAAGGCAGACCACGCTCACGGTGGAaTATCCATGGA
181 ----------+----------+----------+----------+----------+----------+ 240
    TCGCGGTTCACTCTCAGTCGAACGCTTCCGTCTGGTGCGAGTGCCACCTtATAGGTACCT

R  Q  V  R  V  S  L  R  R  Q  T  T  L  T  V  E  Y  P  W  R -

GGTACGGAGCCTTGTTACCAACCTCTAACCGCAGAACTGGGATGTGGGGCTGGAAGTGCC
241 ----------+----------+----------+----------+----------+----------+ 300
    CCATGCCTCGGAACAATGGTTGGAGATTGGCGTCTTGACCCTACACCCCGACCTTCACGG
```

FIG. 9B

```
              Y   G   A   L   L   P       S   N   R   R   T   G   M   W   G   W   K   C   L -
                      K
                      s
                      p
                      6
                      3                                               H
                      2                                               a
                      I                                               e
                                                                      I
      TCCTCTTCTGGGCTGTGCTGGTCACAGCCACTCTCTGCACTGCCAGGCCAGCCCCAACCT
301   ---------+---------+---------+---------+---------+---------+ 360
      AGGAGAAGACCCGACACGACCAGTGTCGGTGAGAGACGTGACGGTCCGGTCGGGGTTGGA

L   F   W   A   V   L   V   T   A   T   L   C   T   A   R   P   A   P   T   L -
                          E
                          s
                          p
                          I
      TGCCCGAACAAGCTCAGCCCTGGGGAGTCCCTGTGGAAGTGGAGTCTCTCCTGGTCCACC
361   ---------+---------+---------+---------+---------+---------+ 420
      ACGGGCTTGTTCGAGTCGGGACCCCTCAGGGACACCTTCACCTCAGAGAGGACCAGGTGG

P   E   Q   A   Q   P   W   G   V   P   V   E   V   E   S   L   L   V   H   P -
                              B
                              s
                              p                                   N
                              M                                   r
                              I                                   u
                                                                  I
      CTGGCGACCTGCTACAGCTTCGCTGTCGGCTTCGCGATGATGTGCAGAGCATCAACTGGC
421   ---------+---------+---------+---------+---------+---------+ 480
      GACCGCTGGACGATGTCGAAGCGACAGCCGAAGCGCTACTACACGTCTCGTAGTTGACCG

G   D   L   L   Q   L   R   C   R   L   R   D   D   V   Q   S   I   N   W   L -
                              N
                              sP
                              pv
                              Bu
                              II
                              II
                              /
      TksGGGATGGGGTGCAGCTGGTGGAGAGCAACCGTACCCGCATCACAGGGGAGGAGGTGG
481   ---------+---------+---------+---------+---------+---------+ 540
      AmsCCCTACCCCACGTCGACCACCTCTCGTTGGCATGGGCGTAGTGTCCCCTCCTCCACC

?   D   G   V   Q   L   V   E   S   N   R   T   R   I   T   G   E   E   V   E -
                                  N
                                  s
                                  p               H
                                  B               a
                                  I               e
                                  I               I
      AGGTGCGGGACTCCATCCCCGCTGACTCTGGCCTCTACGCTTGCGTGACCAGCAGCCCCT
541   ---------+---------+---------+---------+---------+---------+ 600
      TCCACGCCCTGAGGTAGGGGCGACTGAGACCGGAGATGCGAACGCACTGGTCGTCGGGGA

V   R   D   S   I   P   A   D   S   G   L   Y   A   C   V   T   S   S   P   S -
      B
      g
      l
      I
                              FIG. 9C
```

```
         CTGGCAGCGATACCACCTACTTCTCCGTCAATGTCTCAGATGCACTCCCATCCTCGGAAG
    601  ------------------------------------------------------------  660
         GACCGTCGCTATGGTGGATGAAGAGGCAGTTACAGAGTCTACGTGAGGTAGGAGCCTTC

G  S  D  T  T  Y  F  S  V  N  V  S  D  A  L  P  S  S  E  D -

ATGATGACGACGACGATGACTCCTCCTCGGAGGAGAAAGAGACGGACAACACCAAACCAA
    661  ------------------------------------------------------------  720
         TACTACTGCTGCTGCTACTGAGGAGGAGCCTCCTCTTTCTCTGCCTGTTGTGGTTTGGTT

D  D  D  D  D  D  S  S  S  E  E  K  E  T  D  N  T  K  P  N -
                                                                    B
                                                                    a
                                                                    n
                                                                    I
         ACCCTGTAGCTCCCTACTGGACATCCCCAGAGAAAATGGAGAAGAAACTGCATCGGGTGC
    721  ------------------------------------------------------------  780
         TGGGACATCGAGGGATGACCTGTAGGGGTCTCTTTTACCTCTTCTTTGACGTAGCCCACG

P  V  A  P  Y  W  T  S  P  E  K  M  E  K  K  L  H  R  V  P -
          B                          B
          s                          s
          p  N                       p
          1  s                       1
          2  p                       2
          8  B                       8
          6  I                       6
          I  I                       I                              T
                                                                    a
                                                                    q
                                                                    I
                                                                    I
         CCGCTGCCAAGACGGTGAAGTTCAAGTGCCCGTCGAGTGGGACACCCAACCCCACTCTGC
    781  ------------------------------------------------------------  840
         GGCGACGGTTCTGCCACTTCAAGTTCACGGGCAGCTCACCCTGTGGGTTGGGGTGAGACG

A  A  K  T  V  K  F  K  C  P  S  S  G  T  P  N  P  T  L  R -
                                          B
                                          s
                                          t
                                          X
                                          I
         GCTGGTTGAAAAATGGCAAAGAGTTTAAGCCTGACCACCGAATTGGAGGCTACAAGGTTC
    841  ------------------------------------------------------------  900
         CGACCAACTTTTTACCGTTTCTCAAATTCGGACTGGTGGCTTAACCTCCGATGTTCCAAG

W  L  K  N  G  K  E  F  K  P  D  H  R  I  G  G  Y  K  V  R -
                                                  G  B
                                                  s  a
                                                  u  n
                                                  I  I
         GCTATGCCACCTGGAGCATCATAATGGATTCTGTGGTGCCTTCTGACAAGGGCAACTACA
    901  ------------------------------------------------------------  960
         CGATACGGTGGACCTCGTAGTATTACCTAAGACACCACGGAAGACTGTTCCCGTTGATGT

Y  A  T  W  S  I  I  M  D  S  V  V  P  S  D  K  G  N  Y  T -
          B                                                A  A
          s                                                h  a
          p                                                a  t
          M                                                I  I
          I                                                I
         CCTGCATCGTGGAGAATGAGTATGGGAGCATCAACCACACCTACCAGCTTGACGTCGTGG
    961  ------------------------------------------------------------  1020
         GGACGTAGCACCTCTTACTCATACCCTCGTAGTTGGTGTGGATGGTCGAACTGCAGCACC
```

FIG. 9D

```
           C   I   V   E   N   E   Y   G   S   I   N   H   T   Y   Q   L   D   V   V   E
                                   E
                                   c
                                   o
                                   5
                                   7
                                   I
      AACGATCTCCGCACCGACCCATCCTTCAGGCAGGGCTGSCTGCCAACAAGACAGTGGCCC
1021  ---------+---------+---------+---------+---------+---------+  1080
      TTGCTAGAGGCGTGGCTGGGTAGGAAGTCCGTCCCGACSGACGGTTGTTCTGTCACCGGG

R   S   P   H   R   P   I   L   Q   A   G   L   ?   A   N   K   T   V   A   L -

TGGGCAGCAATGTGGAGTTCATGTGTAAGGTGTACAGCGATCCsmAGCCTCACATTCAGT
1081  ---------+---------+---------+---------+---------+---------+  1140
      ACCCGTCGTTACACCTCAAGTACACATTCCACATGTCGCTAGGskTCGGAGTGTAAGTCA

G   S   N   V   E   F   M   C   K   V   Y   S   D   P   ?   P   H   I   Q   W -
                                           E
       A                                   c
       l                                   o
       w                                   5
       N                                   7
       I                                   I
      GGCTGAAGCACATCGAGGTGAACGGGAGTAAGATCGGGCCAGACAACTTGCCGTATGTCC
1141  ---------+---------+---------+---------+---------+---------+  1200
      CCGACTTCGTGTAGCTCCACTTGCCCTCATTCTAGCCCGGTCTGTTGAACGGCATACAGG

L   K   H   I   E   V   N   G   S   K   I   G   P   D   N   L   P   Y   V   Q -
                                           E
       X   A           B                   c
       h   l           b                   o           G
       o   w           v                   5           s
       I   N           I                   7           u
       I   I           I                   I           I
      AGATCCTGAAGACTGCTGGAGTTAATACCACCGACAAGGAAATGGAGGTGCTTCATCTAC
1201  ---------+---------+---------+---------+---------+---------+  1260
      TCTAGGACTTCTGACGACCTCAATTATGGTGGCTGTTCCTTTACCTCCACGAAGTAGATG

I   L   K   T   A   G   V   N   T   T   D   K   E   M   E   V   L   H   L   R -
                                                   T
                                                   t
                                                   h
                                                   1
                                                   1       A X
                                                   1       c c
                                                   I       c a
                                                   I       I I
      GGAATGTCTCCTTTGAGGATGCGGGGGAGTATACGTGCTTGGCGGGTAACTCTATCGGAC
1261  ---------+---------+---------+---------+---------+---------+  1320
      CCTTACAGAGGAAACTCCTACGCCCCCTCATATGCACGAACCGCCCATTGAGATAGCCTG

```
                                                                       D
                                                                   G   r   P
                                                                   s   a   s
                                                                   u   I   s
                                                                   I   I   I
     TCTCCCATCACTCTGCATGGTTGACCGTTCTGGAAGCCCTGGAAGAGAGACCAGCTGTGA
1321 ---------+---------+---------+---------+---------+---------+ 1380
     AGAGGGTAGTGAGACGTACCAACTGGCAAGACCTTCGGGACCTTCTCTCTGGTCGACACT

S  H  H  S  A  W  L  T  V  L  E  A  L  E  E  R  P  A  V  M -

TGACCTCACCGCTCTACCTGGAGATCATTATCTACTGCACCGGGGCCTTCCTGATCTCCT
1381 ---------+---------+---------+---------+---------+---------+ 1440
     ACTGGAGTGGCGAGATGGACCTCTAGTAATAGATGACGTGGCCCCGGAAGGACTAGAGGA

T  S  P  L  Y  L ⎡E⎤ I  I  I  Y  C  T  G  A  F  L  I  S  C -
                       ⎣374⎦
                B
                s
                p                K                       K
         N      B1               s                       s
         s      a2               p               B       p
         p      n8               6               a       6
         H      I6               3               n       3
         I      II               2I              I       2I

GCATGTTGGGCTCTGTCATCATCTATAAGATGAAGAGCGGCACCAAGAAGAGCGACTTCC
1441 ---------+---------+---------+---------+---------+---------+ 1500
     CGTACAACCCGAGACAGTAGTAGATATTCTACTTCTCGCCGTGGTTCTTCTCGCTGAAGG

M  L  G  S  V  I  I  Y  K  M  K  S  G  T  K  K  S  D  F  H -
                    B
                    s
                    p
             A      1H
             p      2g    C   BH                    F           G
             a      8i    f   aa                    s           s
             L      6A    r   1e                    p           u
             I      II    I   III                   I           I

ATAGCCAGATGGCTGTGCACAAGCTGGCCAAGAGCATCCCTCTGCGCAGACAGGTAACAG
1501 ---------+---------+---------+---------+---------+---------+ 1560
     TATCGGTCTACCGACACGTGTTCGACCGGTTCTCGTAGGGAGACGCGTCTGTCCATTGTC

S  Q  M  A  V  H  K  L  A  K  S  I  P  L  R  R  Q  V  T  V -

N
         sP
         pv
         Bu                                         G           B
         II                                         s           s
         II                                         u           t
                                                    I           I

TGTCAGCTGACTCCAGTGCATCCATGAACTCTGGGGTTCTCCTGGTTCGGCCCTCACGGC
1561 ---------+---------+---------+---------+---------+---------+ 1620
     ACAGTCGACTGAGGTCACGTAGGTACTTGAGACCCCAAGAGGACCAAGCCGGGAGTGCCG

S  A  D  S  S  A  S  M  N  S  G  V  L  L  V  R  P  S  R  L -

B
                                                    s
             N                                      p
             s    DP                                B1    H   BX
             p    rp   P                            a2GAgS    ah
             B    au   s              FIG. 9F      n8soia    mo
```

```
                         I  IM  s                              I6UcAc HI
                         I  II  I                              IIIIII II
                           /                                   // //  /
       TCTCCTCCAGCGGGACCCCCATGCTGGCTGGAGTCTCCGAATATGAGCTCCCTGAGGATC
1621   ---------+---------+---------+---------+---------+---------+ 1680
       AGAGGAGGTCGCCCTGGGGGTACGACCGACCTCAGAGGCTTATACTCGAGGGACTCCTAG

S  S  S  G  T  P  M  L  A  G  V  S  E  Y  E  L  P  E  D  P -

N
          s
          P
          B                                                       B
          I                                                       s
          I                                                       p
                                                                  M
                                                                  I
       CCCGCTGGGAGCTGCCACGAGACAGACTGGTCTTAGGCAAACCACTTGGCGAGGGCTGCT
1681   ---------+---------+---------+---------+---------+---------+ 1740
       GGGCGACCCTCGACGGTGCTCTGTCTGACCAGAATCCGTTTGGTGAACCGCTCCCGACGA

R  W  E  L  P  R  D  R  L  V  L  G  K  P  L  G  E  G  C  F -

B
                         H  s
                         a  t
                         e  X
                         I  I
       TCGGGCAGGTGGTGTTGGCTGAGGCCATCGGGCTGGATAAGGACAAACCCAACCGTGTGA
1741   ---------+---------+---------+---------+---------+---------+ 1800
       AGCCCGTCCACCACAACCGACTCCGGTAGCCCGACCTATTCCTGTTTGGGTTGGCACACT

G  Q  V  V  L  A  E  A  I  G  L  D  K  D  K  P  N  R  V  T -

G                                             DP         X
          Cd                     M                      rp  P      Mh
          fi                     m                      au  s      mo
          rI                     e                      IM  s      eI
          II                     I                      II  I      II
           /                                             /
       CCAAAGTGGCCGTGAAGATGTTGAAGTCCGACGCAACGGAGAAGGACCTGTCGGATCTGA
1801   ---------+---------+---------+---------+---------+---------+ 1860
       GGTTTCACCGGCACTTCTACAACTTCAGGCTGCGTTGCCTCTTCCTGGACAGCCTAGACT

K  V  A  V  K  M  L  K  S  D  A  T  E  K  D  L  S  D  L  I -

TCTCGGAGATGGAGATGATGAAAATGATTGGGAAGCACAAGAATATCATCAACCTTCTGG
1861   ---------+---------+---------+---------+---------+---------+ 1920
       AGAGCCTCTACCTCTACTACTTTTACTAACCCTTCGTGTTCTTATAGTAGTTGGAAGACC

S  E  M  E  M  M  K  M  I  G  K  H  K  N  I  I  N  L  L  G -

B
                      s
                      p
          A           1H
          p           2g
          a           8i
          L           6A
          I           II
           /
       GAGCGTGCACACAGGATGGTCCTCTTTATGTCATTGTGGAGTACGCCTCCAAAGGCAATC
1921   ---------+---------+---------+---------+---------+---------+ 1980
       CTCGCACGTGTGTCCTACCAGGAGAAATACAGTAACACCTCATGCGGAGGTTTCCGTTAG

```
                                                    c                       s
                                                    a                       u
                                                    I                       I
     TCCGGGAGTATCTACAGGCCCGGAGGNCTCCTGGGCTGGAGTACTGCTATAACCCCAGCC
1981 ----------+----------+----------+----------+----------+----------+ 2040
     AGGCCCTCATAGATGTCCGGGCCTCCNGAGGACCCGACCTCATGACGATATTGGGGTCGG

R  E  Y  L  Q  A  R  R  ?  P  G  L  E  Y  C  Y  N  P  S  H -

N
              B          sP           BX   B
              b          pv           gh   s
          A   b          pv           gh   s
          v   b          Bu           lo   t                        A
          a   I          II           II   X                        v
          I   I          II           II   I                        a
                                                                    I
     ACAACCCCGAGGAACAGCTGTCTTCCAAAGATCTGGTATCCTGTGCCTATCAGGTGGCTC
2041 ----------+----------+----------+----------+----------+----------+ 2100
     TGTTGGGGCTCCTTGTCGACAGAAGGTTTCTAGACCATAGGACACGGATAGTCCACCGAG

N  P  E  E  Q  L  S  S  K  D  L  V  S  C  A  Y  Q  V  A  R -

E
                                    c
                                  AXo
                                  cc3
                                  cal
                                  III
     GGGGCATGGAGTATCTTGCCTCTAAGAAGTGTATACACCGAGACCTGGCTGCTAGGAACG
2101 ----------+----------+----------+----------+----------+----------+ 2160
     CCCCGTACCTCATAGAACGGAGATTCTTCACATATGTGGCTCTGGACCGACGATCCTTGC

G  M  E  Y  L  A  S  K  K  C  I  H  R  D  L  A  A  R  N  V -

B
         s
         t                T                       E    AXS
         E                a                       s    vhc
         I                q                       p    aoi
         I                I                       I    III
     TCCTGGTGACCGAGGATAACGTAATGAAGATCGCAGACTTTGGCTTAGCTCGAGACATTC
2161 ----------+----------+----------+----------+----------+----------+ 2220
     AGGACCACTGGCTCCTATTGCATTACTTCTAGCGTCTGAAACCGAATCGAGCTCTGTAAG

L  V  T  E  D  N  V  M  K  I  A  D  F  G  L  A  R  D  I  H -

T
                                                                    t
                              CX                                    h
                              GEm                                   I
                              CdraN                                 1
                              filIa                                 1
                              rIOIe                                 1
                              IIIII                                 I
     ATCATATCGACTACTACAAGAAAACCACCAACGGCCGGCTGCCTGTGAAGTGGATGGCCC
2221 ----------+----------+----------+----------+----------+----------+ 2280
     TAGTATAGCTGATGATGTTCTTTTGGTGGTTGCCGGCCGACGGACACTTCACCTACCGGG

```
          I I                I
          CTGAGGCGTTGTTTGACCG TCTACACACACCAGAGCGATGTGTGGTCTTTTGGAGTGC
    2281  ----------+----------+----------+----------+----------+----------+ 2340
          GACTCCGCAACAAACTGGCC TAGATGTGTGTGGTCTCGCTACACACCAGAAAACCTCACG

E   A   L   F   D   R   I   Y   T   H   Q   S   D   V   W   S   F   G   V   L  -

B
          s
          p
          1H        BXT
          2g        gha
          8i        loq
          6A        III
          II        III
            /        /
          TCTTGTGGGAGATCTTCACTCTGGGTGGCTCCCCATACCCCGGTSTGCCTGTGGAGGAAC
    2341  ----------+----------+----------+----------+----------+----------+ 2400
          AGAACACCCTCTAGAAGTGAGACCCACCGAGGGGTATGGGGCCASACGGACACCTCCTTG

L   W   E   I   F   T   L   G   G   S   P   Y   P   G   ?   P   V   E   E   L  -

E
                                       c                    A
                                       o                    l
                                       5                    w
                                       7                    N
                                       I                    I
          TTTTCAAGCTGCTGAAGGAGGGTCATCGAATGGACAAGCCCAGTAACTGTACCAATGAGC
    2401  ----------+----------+----------+----------+----------+----------+ 2460
          AAAAGTTCGACGACTTCCTCCCAGTAGCTTACCTGTTCGGGTCATTGACATGGTTACTCG

F   K   L   L   K   E   G   H   R   M   D   K   P   S   N   C   T   N   E   L  -

B
                                                               s
                                                               pE
                                       N                       1c
                                       sS                      2o
                                       pp                      83
                                       Hh                      61
                                       II                      II
                                        /
          TGTACATGATGATGCGCGACTGCTGGCATGCAGTGCCCTCTCAGAGACCTACGTTCAAGC
    2461  ----------+----------+----------+----------+----------+----------+ 2520
          ACATGTACTACTACGCGCTGACGACCGTACGTCACGGGAGAGTCTCTGGATGCAAGTTCG

Y   M   M   M   R   D   C   W   H   A   V   P   S   Q   R   P   T   F   K   Q  -

T
                         t
                         h
                         1    B
                         1    b                H
                         1    v                a
                         I    I                e
                         I    I                I
          AGTTGGTGGAAGACCTGGACCGCATTGTGGCCTTGACCTCCAACCAGGAGTATCTGGACC
    2521  ----------+----------+----------+----------+----------+----------+ 2580
          TCAACCACCTTCTGGACCTGGCGTAACACCGGAACTGGAGGTTGGTCCTCATAGACCTGG

```
                  Bs                                        T           Din
              M   sp                                        a           a2gS
              m   tB              C                         q           n8Ia
              e   XI              a                         I           I6Ac
              I   II              I                         I           III
                  /                                                     ///
     TGTCCATACCGCTGGACCAGTACTCACCCAGCTTTCCCGACACACGGAGCTCCACCTGCT
2581 ---------+---------+---------+---------+---------+---------+ 2640
     ACAGGTATGGCGACCTGGTCATGAGTGGGTCGAAAGGGCTGTGTGCCTCGAGGTGGACGA

S  I  P  L  D  Q  Y  S  P  S  F  P  D  T  R  S  S  T  C  S -

B
                                                              s
                         T                                    p
                         t                                    Bl
              B     B    h                  B                 a2
              As    b    l                  s             A   n8
              op    v    l                  p             o   I6
              cM    I    I                  H             c   II
              II    I    I                  I             I   /
     CCTCAGGGGAGGACTCTGTCTTCTCTCATGAGCCGTTACCTGAGGAGCCCTGTCTGCCTC
2641 ---------+---------+---------+---------+---------+---------+ 2700
     GGAGTCCCCTCCTGAGACAGAAGAGAGTACTCGGCAATGGACTCCTCGGGACAGACGGAG

S  G  E  D  S  V  F  S  H  E  P  L  P  E  E  P  C  L  P  R -

T                H
                                     a                a
                                     q                e
                                     I                I
                                     I                I
     GACACCCCACCCAGCTTGCCAACAGTGGACTCAAACGGCGCTGACTACCAACCCTGTCCC
2701 ---------+---------+---------+---------+---------+---------+ 2760
     CTGTGGGGTGGGTCGAACGGTTGTCACCTGAGTTTGCCGCGACTGATGGTTGGGACAGGG

H  P  T  Q  L  A  N  S  G  L  K  R  R  *  L  P  T  L  S  P -

B
                          s
                          p
                          1
                          2M                                T
                          8m                                a
                          6e                                q
                          II                                I
                                                            I
     CAGTTTTCTCCCATTCCGTCGTCACCCGTGCCCCTCACCCACAATCCCCTTGTTGGACAC
2761 ---------+---------+---------+---------+---------+---------+ 2820
     GTCAAAAGAGGGTAAGGCAGCAGTGGGCACGGGGAGTGGGTGTTAGGGGAACAACCTGTG

V  F  S  H  S  V  V  T  R  A  P  H  P  Q  S  P  C  W  T  H

A      E
                                             l      c
                            H                w      o              HS
                            a                N      N              at
                            e                I      I              eu
                            I                                      II
                                                                   /
     ACTGCCTTTCTCCTCCTCCTTTTcgCGCTGGgAAGAGgCcAGTGCCTGACTGAGGCCTTC
2821 ---------+---------+---------+---------+---------+---------+ 2880
     TGACGGAAAGAGGAGGAGGAAAagcGCGACCgTTCTCcGgTCACGGACTGACTCCGGAAG

```
                                                    p         p
                                                    6         6
                                                    3         3
                                                    2         2
                                                    I         I
      CTGTGTTGTGGGCCTTCCCCCTCCATCACCCCCAAGACCCCTCTTCTCCCTCTTCTTAGC
2881  ----------+---------+---------+---------+---------+---------+  2940
      GACACAACACCCGGAAGGGGGAGGTAGTGGGGGTTCTGGGGAGAAGAGGGAGAAGAATCG

V  L  W  A  F  P  L  H  H  P  Q  D  P  S  S  P  S  S  *  P -

T
                         t
                         h
              B          l                          X
              s          l                          Gm
              p          l                          Cda     M
              M          I                          fiI     m
              I          I                          rII     e
                                                    III     I
                                                    //
      CTGCTGTGTGAGAGAGGAGCCAAGAGGCAGGTGCTTGCCGACGGCCGCATCCTCCTTCCC
2941  ----------+---------+---------+---------+---------+---------+  3000
      GACGACACACTCTCTCCTCGGTTCTCCGTCCACGAACGGCTGCCGGCGTAGGAGGAAGGG

A  V  *  E  R  S  Q  E  A  G  A  C  R  R  P  H  P  P  S  Q -

T
                                t
                          N     h
              P           s     l
              f           p     l
              l           B     l
              M           I     I
              I           I     I
      AGGTGTTGGACCAAGACCCGSCCCGCTGCCTGGCACTGCTTGGAGGTGTGCAGAGCGGAA
3001  ----------+---------+---------+---------+---------+---------+  3060
      TCCACAACCTGGTTCTGGGCSGGGCGACGGACCGTGACGAACCTCCACACGTCTCGCCTT

V  L  D  Q  D  P  ?  R  C  L  A  L  L  G  G  V  Q  S  G  S -

H
                                i
              B                 n
              s                 c
              m                 I
              I                 I
      GCAAGTGGAGSATCCGGGGCATTCCTGTTGACCCATCAGCCCCTTCTGTTCTGGCGGcAG
3061  ----------+---------+---------+---------+---------+---------+  3120
      CGTTCACCTCSTAGGCCCCGTAAGGACAACTGGGTAGTCGGGGAAGACAAGACCGCCgTC

K  W  P  I  R  G  I  P  V  D  P  S  A  P  S  V  L  A  A  G

B
                        s
                        p
              D         Bl
              r    PS   a2                    HS        G
              a    st   n8                    at        s
              I    sy   I6                    eu        u
              I    II   II                    II        I
                  /    /                     /
      GGGCCTTGGGGCTCCTGGAAGCCGTGAGGTTTCTGTTTAGGCCTTACCGAAGGCAaCCTC
3121  ----------+---------+---------+---------+---------+---------+  3180
      CCCGGAACCCCGAGGACCTTCGGCACTCCAAAGACAAATCCGGAATGGCTTCCGTtGGAG

A  L  G  L  L  E  A  V  R  F  L  F  R  P  Y  R  R  Q  P  L -
```

```
                              A
                              s
                     B        p
                     s        7B        K
                     t        1a        p
                     X        8n        n
                     I        II        I
                     /
         TGCTCCAGATGGATGGTACCAGTAGCTTCTTAATTCCAATACTAATTTGCTTTGCTGACC
3181     ------------+---------+---------+---------+---------+---------+ 3240
         ACGAGGTCTACCTACCATGGTCATCGAAGAATTAAGGTTATGATTAAACGAAACGACTGG

L  Q  M  D  G  T  S  S  F  L  I  P  I  L  I  C  F  A  D  Q  -

B
              A                                                         s
              s                                                         p
              p  B              B              A                        1
              7Bs  K            b              l                        2S
              1ap  p            v              w                        8t
              8nM  n            I              N                        6y
              III  I            I              I                        II
              //                                                        /
         AAATACCTGCCTGGTACCAGAAGACAGGGAGGCAGAGACTGGGAGCCGTGATGTGCCCTT
3241     ---------+---------+---------+---------+---------+---------+- 3300
         TTTATGGACGGACCATGGTCTTCTGTCCCTCCGTCTCTGACCCTCGGCACTACACGGGAA

I  P  A  W  Y  Q  K  T  G  R  Q  R  L  G  A  V  M  C  P  W  -

B              B
                        s              s
                        p              p              D
                        B1             B1             r
                E       a2             a2             a
                s       n8             n8             I
                p       I6             I6             I
                I       II             II             I
                        /              /
         GGgCTGAGCCCTAGACTTGGGGCTCTGTACATAGCTATGAAGAAAAACACAAAGTGTATA
3301     ---------+---------+---------+---------+---------+---------+ 3360
         CCcGACTCGGGATCTGAACCCCGAGACATGTATCGATACTTCTTTTTGTGTTTCACATAT

A  E  P  *  T  W  G  S  V  H  S  Y  E  E  K  H  K  V  Y  K  -

A
                        f     N
                        l     s        D                        DNS
                        I     p        r                        sct
                        I     H        a                        apy
                        I     I        I                        III
                                                                //
         AATCTTGAGTATATATTTACATGTCTTTTTAAAAAGGGTCGTTACTAGAGATTTACCATG
3361     ---------+---------+---------+---------+---------+---------+ 3420
         TTAGAACTCATATATAAATGTACAGAAAAATTTTTCCCAGCAATGATCTCTAAATGGTAC

S  *  V  Y  I  Y  M  S  F  *  K  G  S  L  L  E  I  Y  H  G  -

A
              h
              a
              I
              I
         GGGGAGACGCCCAGGGTAGCATCCGTTGCTATATATTAAAAACAAACGAACAGAAAAAAA
3421     ---------+---------+---------+---------+---------+---------+ 3480
         CCCCTCTGCGGGTCCCATCGTAGGCAACGATATATAATTTTTGTTTGCTTGTCTTTTTTT
```

AXS
                        vhc
                        aoi
                        III
                         /
        AAAAAAAAAAAACTCGAGGGGGG
3481    ------------+---------  3503
        TTTTTTTTTTTGAGCTCCCCCC

K   K   K   L   E   G   G   -
```

Enzymes that do cut:

| AatII   | AccI    | AflIII   | AhaII   | AlwNI   | AocI    | ApaLI   | Asp718I |
|---------|---------|----------|---------|---------|---------|---------|---------|
| AvaI    | BalI    | BamHI    | BanI    | BanII   | BbeI    | BbvII   | BglI    |
| BglII   | BsmI    | Bsp1286I | BspHI   | BspMI   | BstEII  | BstXI   | CfrI    |
| Cfr10I  | DraI    | DraII    | DraIII  | DsaI    | Eco31I  | Eco57I  | Eco78I  |
| EcoNI   | EcoRI   | EspI     | FspI    | GdiII   | GsuI    | HaeI    | HaeII   |
| HgiAI   | HincII  | KpnI     | Ksp632I | MmeI    | NaeI    | NarI    | NcoI    |
| NruI    | NspBII  | NspHI    | PflMI   | PpuMI   | PssI    | PvuII   | SacI    |
| SacII   | ScaI    | SciI     | SmaI    | SphI    | StuI    | StyI    | TaqII   |
| Tth111I | Tth111II| XcaI     | XhoI    | XhoII   | XmaI    | XmaIII  |         |

Enzymes that do not cut:

| AflII  | ApaI    | Asp700I | AsuII   | AvrII   | BclI    | BspMII  | BssHII |
|--------|---------|---------|---------|---------|---------|---------|--------|
| ClaI   | Eco47III| EcoRV   | HgiEII  | HindIII | HpaI    | MfeI    | MluI   |
| NdeI   | NheI    | NotI    | NsiI    | PmaCI   | PstI    | PvuI    | RsrII  |
| SalI   | SfiI    | SnaBI   | SpeI    | SplI    | SspI    | VspI    | XbaI   |

FIG. 9M

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 3503

```
                    ( B ) TYPE: nucleic acid
                    ( C ) STRANDEDNESS: single
                    ( D ) TOPOLOGY: linear ( x i ) SEQUENCE DESCRIPTION: SEQ ID NO: 1:

GGAATTCGGC  ACGAGCGCCC  GGGCTGGAGG  CGCCCGGCTC  GGAGTGCCGC  CGGGAGTCGT      60

GCCTCGGCCG  CGGAGCCCTC  GAGACCCCAT  CAGGATCTGA  ACGGAGCCCG  GAGACGAGCG     120

GCGGGACGCA  AGACACAGAC  ACCCSCCSCG  CCACGGACAG  CTCTCCAGAG  GCGGGACCGC     180

AGCGCCAAGT  GAGAGTCAGC  TTGCGAAGGC  AGACCACGCT  CACGGTGGAA  TATCCATGGA     240

GGTACGGAGC  CTTGTTACCA  ACCTCTAACC  GCAGAACTGG  G ATG TGG GGC TGG AAG     296
                                                 Met Trp Gly Trp Lys
                                                  1               5

TGC CTC CTC TTC TGG GCT GTG CTG GTC ACA GCC ACT CTC TGC ACT GCC         344
Cys Leu Leu Phe Trp Ala Val Leu Val Thr Ala Thr Leu Cys Thr Ala
             10              15              20

AGG CCA GCC CCA ACC TTG CCC GAA CAA GCT CAG CCC TGG GGA GTC CCT         392
Arg Pro Ala Pro Thr Leu Pro Glu Gln Ala Gln Pro Trp Gly Val Pro
             25              30              35

GTG GAA GTG GAG TCT CTC CTG GTC CAC CCT GGC GAC CTC CTA CAG CTT         440
Val Glu Val Glu Ser Leu Leu Val His Pro Gly Asp Leu Leu Gln Leu
             40              45              50

CGC TGT CGG CTT CGC GAT GAT GTG CAG AGC ATC AAC TGG CTK SGG GAT         488
Arg Cys Arg Leu Arg Asp Asp Val Gln Ser Ile Asn Trp Xaa Xaa Asp
 55              60              65

GGG GTG CAG CTG GTG GAG AGC AAC CGT ACC CGC ATC ACA GGG GAG GAG         536
Gly Val Gln Leu Val Glu Ser Asn Arg Thr Arg Ile Thr Gly Glu Glu
 70              75              80              85

GTG GAG GTG CGG GAC TCC ATC CCC GCT GAC TCT GGC CTC TAC GCT TGC         584
Val Glu Val Arg Asp Ser Ile Pro Ala Asp Ser Gly Leu Tyr Ala Cys
             90              95             100

GTG ACC AGC AGC CCC TCT GGC AGC GAT ACC ACC TAC TTC TCC GTC AAT         632
Val Thr Ser Ser Pro Ser Gly Ser Asp Thr Thr Tyr Phe Ser Val Asn
         105             110             115

GTC TCA GAT GCA CTC CCA TCC TCG GAA GAT GAT GAC GAT GAC CAT GAC         680
Val Ser Asp Ala Leu Pro Ser Ser Glu Asp Asp Asp Asp Asp His Asp
         120             125             130

TCC TCC TCG GAG GAG AAA GAG ACG GAC AAC ACC AAA CCA AAC CCT GTA         728
Ser Ser Ser Glu Glu Lys Glu Thr Asp Asn Thr Lys Pro Asn Pro Val
 135             140             145

GCT CCC TAC TGG ACA TCC CCA GAG AAA ATG GAG AAG AAA CTG CAT CGG         776
Ala Pro Tyr Trp Thr Ser Pro Glu Lys Met Glu Lys Lys Leu His Arg
 150             155             160             165

GTG CCC GCT GCC AAG ACG GTG AAG TTC AAG TGC CCG TCG AGT GGG ACA         824
Val Pro Ala Ala Lys Thr Val Lys Phe Lys Cys Pro Ser Ser Gly Thr
             170             175             180

CCC AAC CCC ACT CTG CGC TGG TTG AAA AAT GGC AAA GAG TTT AAG CCT         872
Pro Asn Pro Thr Leu Arg Trp Leu Lys Asn Gly Lys Glu Phe Lys Pro
             185             190             195

GAC CAC CGA ATT GGA GGC TAC AAG GTT CGC TAT GCC ACC TGG AGC ATC         920
Asp His Arg Ile Gly Gly Tyr Lys Val Arg Tyr Ala Thr Trp Ser Ile
         200             205             210

ATA ATG GAT TCT GTG GTG CCT TCT GAC AAG GGC AAC TAC ACC TGC ATC         968
Ile Met Asp Ser Val Val Pro Ser Asp Lys Gly Asn Tyr Thr Cys Ile
 215             220             225

GTG GAG AAT GAG TAT GGG AGC ATC AAC CAC ACC TAC CAG CTT GAC GTC        1016
Val Glu Asn Glu Tyr Gly Ser Ile Asn His Thr Tyr Gln Leu Asp Val
 230             235             240             245

GTG GAA CGA TCT CCG CAC CGA CCC ATC CTT CAG GCA GGG CTG SCT GCC        1064
Val Glu Arg Ser Pro His Arg Pro Ile Leu Gln Ala Gly Leu Xaa Ala
             250             255             260
```

| | | | | | | | | | | | | | | | | |
|---|---|---|---|---|---|---|---|---|---|---|---|---|---|---|---|---|
| AAC | AAG | ACA | GTG | GCC | CTG | GGC | AGC | AAT | GTG | GAG | TTC | ATG | TGT | AAG | GTG | 1112 |
| Asn | Lys | Thr | Val | Ala | Leu | Gly | Ser | Asn | Val | Glu | Phe | Met | Cys | Lys | Val | |
| | | | 265 | | | | 270 | | | | | 275 | | | | |
| TAC | AGC | GAT | CCS | MAG | CCT | CAC | ATT | CAG | TGG | CTG | AAG | CAC | ATC | GAG | GTG | 1160 |
| Tyr | Ser | Asp | Xaa | Xaa | Pro | His | Ile | Gln | Trp | Leu | Lys | His | Ile | Glu | Val | |
| | | 280 | | | | | 285 | | | | | 290 | | | | |
| AAC | GGG | AGT | AAG | ATC | GGG | CCA | GAC | AAC | TTG | CCG | TAT | GTC | CAG | ATC | CTG | 1208 |
| Asn | Gly | Ser | Lys | Ile | Gly | Pro | Asp | Asn | Leu | Pro | Tyr | Val | Gln | Ile | Leu | |
| | 295 | | | | | 300 | | | | | 305 | | | | | |
| AAG | ACT | GCT | GGA | GTT | AAT | ACC | ACC | GAC | AAG | GAA | ATG | GAG | GTG | CTT | CAT | 1256 |
| Lys | Thr | Ala | Gly | Val | Asn | Thr | Thr | Asp | Lys | Glu | Met | Glu | Val | Leu | His | |
| 310 | | | | | 315 | | | | | 320 | | | | | 325 | |
| CTA | CGG | AAT | GTC | TCC | TTT | GAG | GAT | GCG | GGG | GAG | TAT | ACG | TGC | TTG | GCG | 1304 |
| Leu | Arg | Asn | Val | Ser | Phe | Glu | Asp | Ala | Gly | Glu | Tyr | Thr | Cys | Leu | Ala | |
| | | | | 330 | | | | | 335 | | | | | 340 | | |
| GGT | AAC | TCT | ATC | GGA | CTC | TCC | CAT | CAC | TCT | GCA | TGG | TTG | ACC | GTT | CTG | 1352 |
| Gly | Asn | Ser | Ile | Gly | Leu | Ser | His | His | Ser | Ala | Trp | Leu | Thr | Val | Leu | |
| | | | 345 | | | | | 350 | | | | | 355 | | | |
| GAA | GCC | CTG | GAA | GAG | AGA | CCA | GCT | GTG | ATG | ACC | TCA | CCG | CTC | TAC | CTG | 1400 |
| Glu | Ala | Leu | Glu | Glu | Arg | Pro | Ala | Val | Met | Thr | Ser | Pro | Leu | Tyr | Leu | |
| | | 360 | | | | | 365 | | | | | 370 | | | | |
| GAG | ATC | ATT | ATC | TAC | TGC | ACC | GGG | GCC | TTC | CTG | ATC | TCC | TGC | ATG | TTG | 1448 |
| Glu | Ile | Ile | Ile | Tyr | Cys | Thr | Gly | Ala | Phe | Leu | Ile | Ser | Cys | Met | Leu | |
| | 375 | | | | | 380 | | | | | 385 | | | | | |
| GGC | TCT | GTC | ATC | ATC | TAT | AAG | ATG | AAG | AGC | GGC | ACC | AAG | AAG | AGC | GAC | 1496 |
| Gly | Ser | Val | Ile | Ile | Tyr | Lys | Met | Lys | Ser | Gly | Thr | Lys | Lys | Ser | Asp | |
| 390 | | | | | 395 | | | | | 400 | | | | | 405 | |
| TTC | CAT | AGC | CAG | ATG | GCT | GTG | CAC | AAG | CTG | GCC | AAG | AGC | ATC | CCT | CTG | 1544 |
| Phe | His | Ser | Gln | Met | Ala | Val | His | Lys | Leu | Ala | Lys | Ser | Ile | Pro | Leu | |
| | | | | 410 | | | | | 415 | | | | | 420 | | |
| CGC | AGA | CAG | GTA | ACA | GTG | TCA | GCT | GAC | TCC | AGT | GCA | TCC | ATG | AAC | TCT | 1592 |
| Arg | Arg | Gln | Val | Thr | Val | Ser | Ala | Asp | Ser | Ser | Ala | Ser | Met | Asn | Ser | |
| | | | | 425 | | | | | 430 | | | | | 435 | | |
| GGG | GTT | CTC | CTG | GTT | CGG | CCC | TCA | CGG | CTC | TCC | TCC | AGC | GGG | ACC | CCC | 1640 |
| Gly | Val | Leu | Leu | Val | Arg | Pro | Ser | Arg | Leu | Ser | Ser | Ser | Gly | Thr | Pro | |
| | | | 440 | | | | | 445 | | | | | 450 | | | |
| ATG | CTG | GCT | GGA | GTC | TCC | GAA | TAT | GAG | CTC | CCT | GAG | GAT | CCC | CGC | TGG | 1688 |
| Met | Leu | Ala | Gly | Val | Ser | Glu | Tyr | Glu | Leu | Pro | Glu | Asp | Pro | Arg | Trp | |
| | | 455 | | | | | 460 | | | | | 465 | | | | |
| GAG | CTG | CCA | CGA | GAC | AGA | CTG | GTC | TTA | GGC | AAA | CAA | CTT | GGC | GAG | GGC | 1736 |
| Glu | Leu | Pro | Arg | Asp | Arg | Leu | Val | Leu | Gly | Lys | Gln | Leu | Gly | Glu | Gly | |
| 470 | | | | | 475 | | | | | 480 | | | | | 485 | |
| TGC | TTC | GGG | CAG | GTG | GTG | TTG | GCT | GAG | GCC | ATC | GGG | CTG | GAT | AAG | GAC | 1784 |
| Cys | Phe | Gly | Gln | Val | Val | Leu | Ala | Glu | Ala | Ile | Gly | Leu | Asp | Lys | Asp | |
| | | | | 490 | | | | | 495 | | | | | 500 | | |
| AAA | CCC | AAC | CGT | GTG | ACC | AAA | GTG | GCC | GTG | AAG | ATG | TTG | AAG | TCC | GAC | 1832 |
| Lys | Pro | Asn | Arg | Val | Thr | Lys | Val | Ala | Val | Lys | Met | Leu | Lys | Ser | Asp | |
| | | | 505 | | | | | 510 | | | | | 515 | | | |
| GCA | ACG | GAG | AAG | GAC | CTG | TCG | GAT | CTG | ATC | TCG | GAG | ATG | GAG | ATG | ATG | 1880 |
| Ala | Thr | Glu | Lys | Asp | Leu | Ser | Asp | Leu | Ile | Ser | Glu | Met | Glu | Met | Met | |
| | | 520 | | | | | 525 | | | | | 530 | | | | |
| AAA | ATG | ATT | GGG | AAG | CAC | AAG | AAT | ATC | ATC | AAC | CTT | CTG | GGA | GCG | TGC | 1928 |
| Lys | Met | Ile | Gly | Lys | His | Lys | Asn | Ile | Ile | Asn | Leu | Leu | Gly | Ala | Cys | |
| | 535 | | | | | 540 | | | | | 545 | | | | | |
| ACA | CAG | GAT | GGT | CCT | CTT | TAT | GTC | ATT | GTG | GAG | TAC | GCC | TCC | AAA | GGC | 1976 |
| Thr | Gln | Asp | Gly | Pro | Leu | Tyr | Val | Ile | Val | Glu | Tyr | Ala | Ser | Lys | Gly | |
| 550 | | | | | 555 | | | | | 560 | | | | | 565 | |
| AAT | CTC | CGG | GAG | TAT | CTA | CAG | GCC | CGG | AGG | NCT | CCT | GGG | CTG | GAG | TAC | 2024 |
| Asn | Leu | Arg | Glu | Tyr | Leu | Gln | Ala | Arg | Arg | Xaa | Pro | Gly | Leu | Glu | Tyr | |
| | | | | 570 | | | | | 575 | | | | | 580 | | |
| TGC | TAT | AAC | CCC | AGC | CAC | AAC | CCC | GAG | GAA | CAG | CTG | TCT | TCC | AAA | GAT | 2072 |

```
Cys Tyr Asn Pro Ser His Asn Pro Glu Gln Leu Ser Ser Lys Asp
            585             590             595

CTG GTA TCC TGT GCC TAT GAC GTG GCT CGG GGC ATG GAG TAT CTT GCC     2120
Leu Val Ser Cys Ala Tyr Asp Val Ala Arg Gly Met Glu Tyr Leu Ala
        600             605             610

TCT AAG AAG TGT ATA CAC CGA GAC CTG GCT GCT AGG AAC GTC CTG GTG     2168
Ser Lys Lys Cys Ile His Arg Asp Leu Ala Ala Arg Asn Val Leu Val
        615             620             625

ACC GAG GAT AAC GTA ATG AAG ATC GCA GAC TTT GGC TTA GCT CGA GAC     2216
Thr Glu Asp Asn Val Met Lys Ile Ala Asp Phe Gly Leu Ala Arg Asp
630             635             640             645

ATT CAT CAT ATC GAC TAC TAC AAG AAA ACC ACC AAC GGG CGG CTG CCT     2264
Ile His His Ile Asp Tyr Tyr Lys Lys Thr Thr Asn Gly Arg Leu Pro
            650             655             660

GTG AAG TGG ATG GCC CCT GAG GCG TTG TTT GAC CGG ATC TAC ACA CAC     2312
Val Lys Trp Met Ala Pro Glu Ala Leu Phe Asp Arg Ile Tyr Thr His
            665             670             675

CAG AGC GAT GTG TGG TCT TTT GGA GTG CTC TTG TGG GAG ATC TTC ACT     2360
Gln Ser Asp Val Trp Ser Phe Gly Val Leu Leu Trp Glu Ile Phe Thr
            680             685             690

CTG GGT GGC TCC CCA TAC CCC GGT STG CCT GTG GAG GAA CTT TTC AAG     2408
Leu Gly Gly Ser Pro Tyr Pro Gly Xaa Pro Val Glu Glu Leu Phe Lys
        695             700             705

CTG CTG AAG GAG GGT CAT CGA ATG GAC AAG CCC AGT AAC TGT ACC AAT     2456
Leu Leu Lys Glu Gly His Arg Met Asp Lys Pro Ser Asn Cys Thr Asn
710             715             720             725

GAG CTG TAC ATG ATG ATG CGC GAC TGC TGG CAT GCA GTG CCC TCT CAG     2504
Glu Leu Tyr Met Met Met Arg Asp Cys Trp His Ala Val Pro Ser Gln
            730             735             740

AGA CCT ACG TTC AAG CAG TTG GTG GAA GAC CTG GAC CGC ATT GTG GCC     2552
Arg Pro Thr Phe Lys Gln Leu Val Glu Asp Leu Asp Arg Ile Val Ala
        745             750             755

TTG ACC TCC AAC CAG GAG TAT CTG GAC CTG TCC ATA CCG CTG GAC CAG     2600
Leu Thr Ser Asn Gln Glu Tyr Leu Asp Leu Ser Ile Pro Leu Asp Gln
        760             765             770

TAC TCA CCC AGC TTT CCC GAC ACA CGG AGC TCC ACC TGC TCC TCA GGG     2648
Tyr Ser Pro Ser Phe Pro Asp Thr Arg Ser Ser Thr Cys Ser Ser Gly
        775             780             785

GAG GAC TCT GTC TTC TCT CAT GAG CCG TTA CCT GAG GAG CCC TGT CTG     2696
Glu Asp Ser Val Phe Ser His Glu Pro Leu Pro Glu Glu Pro Cys Leu
790             795             800             805

CCT CGA CAC CCC ACC CAG CTT GCC AAC AGT GGA CTC AAA CGG CGC         2741
Pro Arg His Pro Thr Gln Leu Ala Asn Ser Gly Leu Lys Arg Arg
            810             815             820

TGACTACCAA CCCTGTCCCC AGTTTTCTCC CATTCCGTCG TCACCCGTGC CCCTCACCCA   2801
CAATCCCCTT GTTGGACACA CTGCCTTTCT CCTCCTCCTT TTCGCGCTGG AAAGAGGCCA   2861
GTGCCTGACT GAGGCCTTCC TGTGTTGTGG GCCTTCCCCC TCCATCACCC CAAGACCCC    2921
TCTTCTCCCT CTTCTTAGCC TGCTGTGTGA GAGAGGAGCC AAGAGGCAGG TGCTTGCCGA   2981
CGGCCGCATC CTCCTTCCCA GGTGTTGGAC CAAGACCCGA CCCGCTGCCT GGCACTGCTT   3041
GGAGGTGTGC AGAGCGGAAG CAAGTGGAGA ATCCGGGGCA TTCCTGTTGA CCCATCAGCC   3101
CCTTCTGTTC TGGCGGCAGG GGCCTTGGGG CTCCTGGAAG CCGTGAGGTT TCTGTTTAGG   3161
CCTTACCGAA GGCAACCTCT GCTCCAGATG GATGGTACCA GTAGCTTCTT AATTCCAATA   3221
CTAATTTGCT TTGCTGACCA AATACCTGCC TGGTACCAGA AGACAGGGAG GCAGAGACTG   3281
GGAGCCGTGA TGTGCCCTTG GGCTGAGCCC TAGACTTGGG GCTCTGTACA TAGCTATGAA   3341
GAAAAACACA AAGTGTATAA ATCTTGAGTA TATATTTACA TGTCTTTTTA AAAGGGTCG    3401
TTACTAGAGA TTTACCATGG GGGAGACGCC CAGGGTAGCA TCCGTTGCTA TATATTAAAA   3461
```

-continued

ACAAACGAAC AGAAAAAAAA AAAAAAAAAA CTCGAGGGGG GG  3503

( 2 ) INFORMATION FOR SEQ ID NO: 2:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( x i ) SEQUENCE DESCRIPTION: SEQ ID NO: 2:

GGTACCAAGC TTACGTAAGA TCTTCCGGA  29

( 2 ) INFORMATION FOR SEQ ID NO: 3:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 3:

GGAGATCTCC CATCACTCTG CATGGTTG  28

( 2 ) INFORMATION FOR SEQ ID NO: 4:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( x i ) SEQUENCE DESCRIPTION: SEQ ID NO: 4:

CGGAAGATCT CTCCAGGTAG AGCG  24

( 2 ) INFORMATION FOR SEQ ID NO: 5:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 5:

CCGAATTCAT CTTCATCATC TCCATCTC  28

CELLS EXPRESSING A SUBSTANTIAL NUMBER OF SURFACE HIGH AFFINITY HBGF RECEPTORS BUT RELATIVELY FEW LOW AFFINITY HBGF BINDING SITES AND SYSTEM FOR ASSAYING BINDING TO HBGF RECEPTOR

BACKGROUND OF THE INVENTION

The field of the invention is heparin-binding growth factors (HBGFs) This work was supported in part by a grant from the U.S. government, which has certain rights in the invention.

The HBGFs are a family of mammalian growth factors related by sequence homology, receptor affinity, and, as their name implies, the ability to bind heparin. Heparin is a glycosaminoglycan (GAG) with anticoagulant activity commercially isolated from mammalian tissues as a heterogeneous mixture of variably sulfated polysaccharide chains (molecular weight 6-30 kDa) composed of repeating units of D-glucosamine and either L-iduronic acid or D-glucuronic acid. Binding to heparin has been shown to stabilize at lease some of the HBGFs against heat denaturation and proteolytic degradation (Gospodarowicz and Chen, J. Cell Physiol. 128:475-484, 1986; Saskela et al., J. Cell. Biol. 107:743-751, 1988).

Members of the HBGF family which have been identified to date include acidic fibroblast growth factor (aFGF), basic FGF (bFGF), int2 and HST (both of which are considered to be oncogenes expressed at abnormally high rates in certain cancers), K-FGF (first seen in a Kaposi's sarcoma), FGF-5, FGF-6, and keratinocyte growth factor (KGF) (Rubin et al., Proc. Natl. Acad. Sci. USA 86:802-806, 1989; Folkman and Klagsbrun, Science 235:442-447, 1987; Klagsbrun, Progress in Growth Factor Research 1:207-235, 1989). The HBGFs stimulate proliferation, migration and differentiation of cells of mesenchymal and neuroectodermal origin. bFGF, one of the more thoroughly studied HBGFs, participates as an autocrine modulator of cell growth and transformation and is a potent angiogenic factor abundant in normal and malignantly transformed cells (Rifkin and Moscatelli, J Cell. Biol. 109:1-6, 1989; Yayon and Klagsbrun, Proc. Natl Acad. Sci. USA 87:5346-5350, 1990). The strong affinity of bFGF for heparin has greatly facilitated the purification and characterization of this growth factor (Shing et al., Science 223:1296-1299, 1984; Klagsbrun and Shing, Proc. Natl. Acad. Sci USA 82:805-809, 1985). Heparin is also a potent modulator of the biological activity of bFGF and aFGF: e.g., heparin has been found to potentiate the mitogenic effect of aFGF on endothelial cells (Thornton et al., Science 222:623-625, 1983). Protamine, a protein that binds avidly to heparin, inhibits the ability of heparin to stimulate endothelial cell migration (Azizkhan et al., J. Exp. Med. 152:931-944, 1980) and inhibits angiogenesis associated with embryogenesis and inflammation (Taylor and Folkman, Nature 297:307-312, 1982).

The biological response of cells to the HBGFs is mediated through specific, high-affinity ($K_d = 2-20 \times 10^{-11}$M) cell surface receptors which possess intrinsic tyrosine kinase activity and are phosphorylated upon binding of an HBGF (Coughlin et al., J. Biol. Chem. 263:988-933, 1988). Several closely related glycoproteins from various species have been denominated FGF receptors: these include the chicken FGF receptor (CEK) and the protein encoded by the human cDNA clone flg, as well as others (Lee et al., Science 245:57-60, 1989; Ruta et al., Oncogene 5:635-643, 1989; Kornbluth et al., Mol. and Cell. Biol. 8:5541-5544, 1988; Pasquale et al., Proc. Natl Acad. Sci. USA 86:5449-5433, 1990; Safran et al., Oncogene 5:635-643, 1990). A lower-affinity ($K_d = 10^{-7} - 10^{-9}$M), large-capacity class of binding sites has also been identified (Moscatelli, J. Cell Biol. 131:123-130, 1987). These low-affinity binding sites are heparan sulfate proteoglycans (HSPGs; a class of protein-linked polysaccharides with a sugar structure similar to heparin, but having more N-acetyl groups and fewer O- and N-sulfate groups than does heparin) found on the cell surface (Moscatelli, J. Cell Biol. 107:753-759, 1988) and in the extra-cellular matrix (Vlodavsky et al., Proc. Natl. Acad. Sci. USA 84:2292-2296, 1987). bFGF can be released from these low-affinity binding sites by an excess of heparin or by enzymatic digestion with heparinases, but not with closely related GAGs such as chondroitin sulfate or by enzymes such as chondroitinase or hyaluronidase (Moscatelli, J. Cell Biol. 107:753-759, 1988; Bashkin et al., Biochem. 28:1737-1743, 1989). Recently, it has been shown that herpes simplex viruses, which are capable of binding to cell surface HSPG (WuDunn and Spear, J. Virol. 63:52-58, 1989), use the high-affinity FGF receptor as a portal of entry into cells (Kaner et al., Science 248:1410-1413, 1990).

SUMMARY OF THE INVENTION

The invention is based upon the discovery that cell surface HSPGs participate as obligatory accessory receptors to permit binding of bFGF to the high-affinity FGF receptors, and that soluble heparin or heparin-like molecules can effectively replace cell surface HSPG in this role. Such an obligatory cooperative interaction of low- and high-affinity FGF receptors represents a novel mechanism for growth factor/receptor interaction and regulation. Recognition of the crucial role of HSPG in FGF-receptor interactions, and of the fact that heparin and heparin-like molecules can substitute for cell-surface HSPG, has led to the design of two types of assays, a cell-based assay and a cell-free assay, intended to screen specifically for substances capable of affecting this trimolecular interaction. The cell-free assay of the invention provides the additional advantage of obviating the need for using cultured cells to assay for such substances, substituting instead a simpler, faster, and inherently more reproducible in vitro method.

The invention features cells (typically in the form of a homogeneous population of cells, such as a clone) having on average (1) a number of cell surface low-affinity HBGF-binding sites per cell less than 20% (and preferably 10% or less) of the number of such binding sites found on wild-type CHO-K1 cells [which are available from the American Type Culture Collection (ATCC, Bethesda, Md.) as Accession No. CCL61], and (2) at least three (and preferably four or more) times the number of cell surface high-affinity HBGF receptors per cell found on such CHO-K1 cells. The high-affinity HBGF receptors expressed on the surfaces of the cells may be naturally endogenous to such cells or arise as the result of a mutation, or may be expressed from a recombinant nucleic acid on a vector either transiently transfected into the cells or incorporated into the genome of each of the cells. Such a nucleic acid may encode a homologous (i.e., derived from the same species as that of the cell) or heterologous (i.e., derived from a species different from that of the cell) high-affinity HBGF receptor. Species in which high-affinity HBGF receptors have been identified and cloned include human, chicken and mouse; it is likely that every species of vertebrate (and possibly invertebrates) will be found to have HBGFs and high-affinity HBGF receptors. Such HBGFs and high-affinity HBGF receptors can be identified and cloned by taking advantage of expected sequence homologies, using methods analogous to those described below. A number of different HBGFs (e.g., aFGF, bFGF, int2, HST, K-FGF, FGF-5, FGF-6, and KGF) have been identified, and it is likely that others exist. Many if not all of those tested, including HBGFs from several species, appear to bind to the same high-affinity receptor proteins thus, a cell of the invention expressing one type of high-affinity HBGF receptor (e.g., an aFGF or a bFGF receptor) may be useful for assays involving a number of different HBGFs.

Given the characteristic affinity of the HBGFs for heparin, it is expected that each HBGF requires heparin or a heparin-like molecule in order to form an affinity complex with a high-affinity HBGF receptor. By heparin-like molecule is meant a polysaccharide capable of substituting for heparin in permitting the binding of an HBGF to a high-affinity HBGF receptor in any one of the assays of the invention. Molecules which have been demonstrated to be "heparin-like" molecules by this definition include highly-sulfated lung-derived heparan sulfate and a 12-sugar heparin fragment (prepared as described by Bashkin et al., Biochemistry 28:1737–1743, 1989). In contrast, under-sulfated sulfated kidney-derived heparan sulfate and a shark cartilage-derived chondroitin sulfate (both purchased from Seikagaku Kogio Co., Tokyo, Japan) did not stimulate the binding of an HBGF to a high-affinity HBGF receptor in an assay of the invention, and thus do not qualify as "heparin-like" molecules. Whether or not a given polysaccharide qualifies as a "heparin-like" molecule can be readily determined by comparison with heparin in the assays described below. It would be expected that polysaccharides capable of releasing HBGFs from subendothelial cell matrix in a manner similar to that of heparin (Bashkin et al., Biochem 28:1737–1743, 1989) would be likely candidates for "heparin-like" molecules.

The cell of the invention may be used as a test cell in a system for assaying the ability of a substance to bind to a high-affinity HBGF receptor, which system also includes an amount of heparin (or a heparin-like molecule) sufficient to induce binding of a HBGF to a high-affinity HBGF on the test cell. The assay would include the steps of combining the substance to be tested with (a) heparin or a heparin-like molecule, and (b) a test cell, and measuring the amount of the substance that binds to high-affinity receptors on the test cell.

The cell of the invention could also be used as a test cell in a system for assaying the ability of a substance to affect the interaction between a given type of HBGF and a high-affinity HBGF receptor, which system would also include the given type of HBGF. The assay would include the steps of combining a first test cell with the given HBGF in the presence of the substance; combining a second test cell with the given HBGF in the absence of the substance; and comparing the amount of the given HBGF bound to the first cell with the amount of the given HBGF bound to the second cell.

Alternatively, each of the above-described methods and assay systems can utilize, instead of the cell of the invention, a molecule including a HBGF-binding portion of a high-affinity HBGF receptor polypeptide, or a hybrid molecule in which a HBGF-binding portion of a high-affinity HBGF receptor polypeptide is covalently linked to an antigenic moiety (a moiety such as a polypeptide which can form an immune complex with an appropriate antibody). The antigenic moiety portion of the hybrid molecule serves as a convenient means of separating bound HBGF from unbound HBGF: only that HBGF which is bound to the hybrid molecule (presumably via the high-affinity HBGF receptor-derived portion of the hybrid molecule) will be immunoprecipitated (or otherwise separated from the assay mixture) with an antibody specific for the antigenic portion of the hybrid molecule.

Also within the invention is a method of separating or isolating an HBGF from a sample (e.g., a biological fluid such as blood or serum), which method includes the steps of (1) providing an affinity compound in which a HBGF-binding portion of a high-affinity HBGF receptor protein is bound to a matrix material, (2) contacting the sample with the affinity compound in the presence of heparin or a heparin-like material to permit formation of affinity complexes between the HBGF and the affinity compound, and (3) separating the affinity complexes from the remainder of the sample. This can be conveniently accomplished if the affinity compound is packed within a column to form an affinity column over which the sample is passed.

Other features and advantages of the invention will be apparent from the following detailed description, and from the claims.

DETAILED DESCRIPTION

The drawings are first described.

BRIEF DESCRIPTION OF THE DRAWINGS

FIG. 9A is a representation of the amino acid sequence deduced from the nucleotide sequence encoding the cloned murine bFGF receptor.

FIGS. 9B–9M together are a representation of the nucleotide sequence encoding the cloned murine bFGF receptor.

THE ASSAY SYSTEMS OF THE INVENTION

Each of the assay systems of the invention provides a convenient means to test various substances for their ability to interfere with or augment the HBGF/HSPG/high-affinity receptor trimolecular binding interaction. A substance which proves able to interfere significantly with this binding interaction would potentially be useful as an antitumor agent: by inhibiting the HBGF's binding to its high-affinity receptor, stimulation by the HBGF of both tumor cell growth and the angiogenesis necessary to ensure nourishment to the growing tumor is halted, and the tumor's growth curtailed. On the other hand, a substance which augments the trimolecular binding interaction would have potential applications as a promoter of beneficial regrowth of tissues, as in wound healing.

THE CELL-BASED ASSAY

The cell-based assay system of the invention utilizes cells which express on their surfaces a substantial number of high-affinity HBGF receptors, but relatively few (if any) low-affinity HBGF binding sites. Such cells may be naturally-occurring cells isolated, e.g., from a natural tissue or from a cultured cell line, or may be cells bearing a mutational defect which causes them to express little if any HSPGs on their surfaces. The cells may naturally express one or more types of high-affinity HBGF receptors, or may be stably or transiently transfected with vectors encoding one or more high-affinity receptors. In the experiments described in Example 1 below, a clone of CHO K1 cells mutationally deficient in cell-surface HSPGs and having a naturally low level of high-affinity HBGF receptors was transfected with a vector encoding the mouse high-affinity bFGF receptor, yielding both a transiently-transfected and a stably-transfected cell line which express the high-affinity bFGF receptor at the cell surface. The usefulness of other cell isolates or cell lines in the assay system of the invention can be determined by the methods described in Example 1.

The cell-based assay system of the invention can be used to assay for substances capable of interfering with or augmenting the HBGF/heparin/high-affinity HBGF receptor trimolecular binding interaction. Standard conditions for such an assay might include 100–200 pM $^{125}$I-bFGF and 100 ng/ml heparin, added to a plate of confluent mutant CHO K1 cells expressing the recombinant receptor on their surfaces. Alternatively, the cell-based assay system of the invention can be used to assay for substances capable of replacing heparin or HBGF in the trimolecular binding interaction. In such an assay, a plate of confluent cells of the invention would be supplied with, e.g., 100–200 pM $^{125}$I-bFGF and either heparin or the substance of interest in a range of concentrations The amount of $^{125}$I bound to the high-affinity receptors on the cells could be analyzed by, for example, the methods described in Example 1 below.

THE CELL-FREE ASSAY

Figure 10:
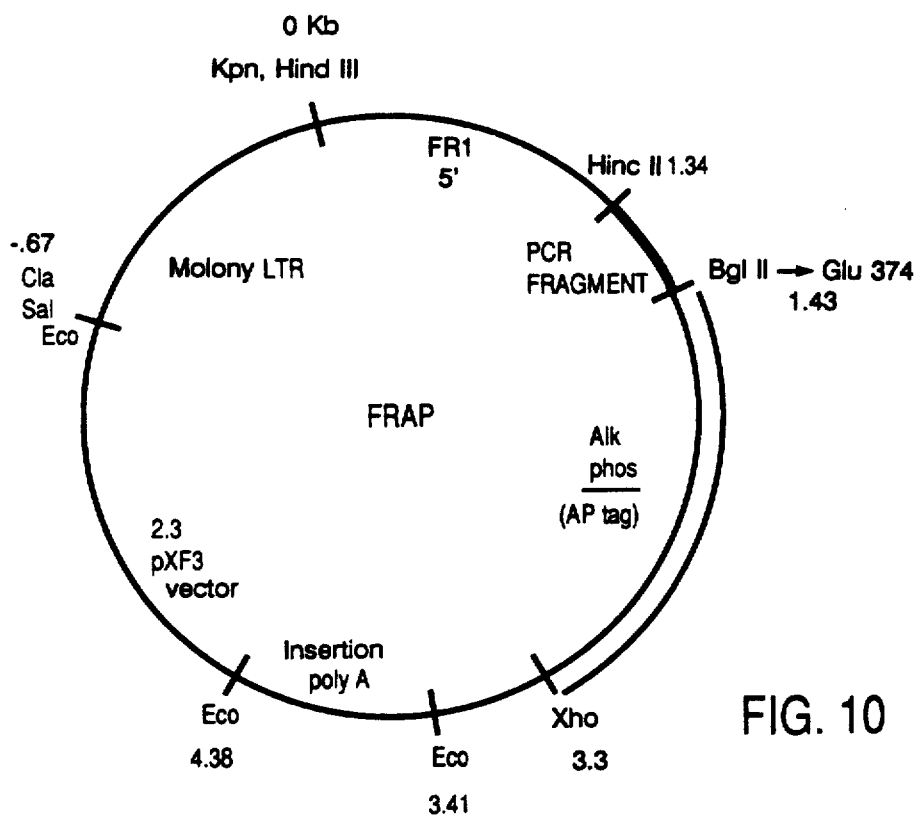
FIG. 10 is a schematic diagram of the FRAP plasmid, indicating the locations of certain restriction sites.

The cell-free assay of the invention utilizes the HBGF-binding portion of a HBGF high-affinity receptor protein to assay for substances which can affect, or replace heparin or HBGF in, the trimolecular interaction. In the experiments described in Example 2 below, a recombinant fusion protein consisting of the portion of the murine bFGF high-affinity receptor protein which is on the amino-terminal side of the cell-membrane-spanning domain (as evidenced by the predominantly hydrophobic amino acid sequence of the latter domain) linked to alkaline phosphatase was expressed from an appropriately-constructed vector, and was found to bind labelled bFGF in the presence but not in the absence of heparin or a heparin-like molecule. Alkaline phosphatase was made a part of the hybrid protein because it simplified screening for and purifying the hybrid protein; other enzymes and/or antigens could readily substitute for alkaline phosphatase, or it could be dispensed with entirely and, with appropriate screening and purification modifications, solely the HBGF-binding portion of a HBGF high-affinity receptor used in the cell-free assay of the invention. Any portion of the HBGF high-affinity receptor protein can be utilized so long as it binds HBGF in the presence and not in the absence of heparin or a heparin-like molecule, and so long as it can be expressed as a cell-free, soluble protein (i.e., lacking most or all of the cell-membrane-spanning hydrophobic domain (amino acid residues 375-395 of the intact mouse bFGF high-affinity receptor protein, the sequence of which is shown in FIG. 10). Such portions of the HBGF high-affinity receptor protein can be produced by well-known techniques of deletion mapping or polymerase chain reaction (PCR) mutagenesis, and then tested for their usefulness in the cell-free assay system of the invention by comparison with the fusion protein described in Example 2, using appropriate modifications of the assay methods described therein.

EXPERIMENTAL INFORMATION

Described in detail below are the cell-based system of the invention (Example 1) and the cell-free system of the invention (Example 2).

EXAMPLE 1: CELL-BASED SYSTEM

Experimental Procedures

Materials

Recombinant human bFGF was a gift from Takeda Inc., Tokyo, Japan. Heparin was obtained from Hepar, Franklin, Ohio Shark cartilage-derived chondroitin sulfate and under-sulfated, kidney-derived heparan sulfate (HS) were purchased from Seikagaku Kogio Co., Tokyo, Japan. A twelve-sugar heparin fragment and a highly-sulfated, lung-derived HS were kindly provided by Dr. Vlodavsky, Hadassah Medical School, Jerusalem, Israel. Heparinase was a generous gift of Ibex Technologies, Montreal, Canada.

Cloning the Murine FGF Receptor

Sequence comparison of the mouse BEK cDNA (mBEK, Kornbluth et al., Mol. and Cell Biol. 8:5541-5544, 1988), the human FLG cDNA (hFLG, Ruta et al., Oncogene 3:9-15, 1988), and the chicken FGF receptor cDNA (CEK1, Pasquale and Singer, Proc. Natl. Acad. Sci. USA 86:5449-5533, 1989) was used to design a pair of PCR primers corresponding to regions highly conserved among the three species. The 5' primer of the pair is GGAGATCTCCCAT-CACTCTGCATGGTTG (SEQ ID NO: 3). The 3' 22 nucleotides of this primer are identical to a 22-nucleotide sequence of both CEK1 (beginning at position 1091 of CEK1, 86 bp 5' to the transmembrane domain of CEK) and hFLG. The 3' primer is CCGAATT-CATCTTCATCATCTCCATCT (SEQ ID NO: 3). The 3' 22 nucleotides of this primer are identical to a second 22-nucleotide sequence of CEK1 (beginning at position 1665 of CEK1), and contain only one mismatch to corresponding 22-nucleotide portions of hFLG and mBEK. These primers were used to amplify a 574 bp fragment from mouse liver and seminal vesicle first strand cDNA (prepared using a Boehringer Mannheim Biochemicals cDNA synthesis kit). The amplified PCR fragments were subcloned into pGEM7Zf (Promega). Sequence comparison between this PCR clone and CEK1, hFLG and mBEK revealed 84%, 90%, and 74% sequence identity, respectively, consistent with this clone's representing the mouse homologue of the FGF receptor gene, and mBEK's being a closely related cDNA. We refer to this 574 bp probe and subsequent clones as mFR, for "mouse FGF receptor". This probe was then used to screen 300,000 plaques from a murine Balb/c cDNA library in Lambda ZAP (Stratagene, La Jolla, Calif.). Twelve of approximately 100 hybridizing plaques were examined. One of these contained a 3.5 kb insert which, by sequence comparison to CEK1, was determined to encode a full-length FGF receptor with approximately 84% nucleotide identity to CEK1, over the open reading frame. Sequence comparison of mFR (the sequence of which is shown in FIG. 9) and a subsequently-published murine FGF receptor (Reid et al., Proc. Natl. Acad. Sci. USA 87:1596-1600, 1990) revealed nearly 100% identity: mFR contains the 5' 267 bp domain and is missing the six nucleotides coding for amino acids 148 and 149, variants also observed by Reid et al.

Figure 2:
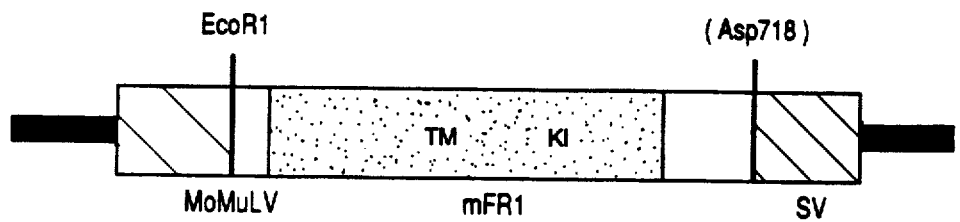
FIG. 2 is a schematic diagram of the mouse FGF receptor expression vector Mo/mFR/SV, in which "TM" represents the transmembrane domain; "KI" represents the tyrosine kinase domain; "SV" represents the SV40 splice and polyadenylation sequences; the stippled region represents the coding sequence and the solid bar represents the bluescript SK vector.

To express mFR in tissue culture, the plasmid Mo/mFR/SV was constructed. Using standard methods, a 3.2 kb EcoR1-Asp 718 restriction fragment from mFR was cloned downstream from the 675 bp Mo-MuLVLTR (Shinnick et al., Nature 293:543-548, 1981) and upstream of the SV40 splice and polyadenylation sequences (Seed, Nature 329:840-842, 1987) in the bluescript-SK vector (Stratagene), as shown in FIG. 2. This sequence contains 282 bp of the 5' untranslated sequence and 453 bp 3' of the mFR termination codon.

Cell Lines and Transfection

The following cell lines were used: Balb/c fibroblasts; NIH 3T3 cells; CHO K1 cells (parental wild-type CHO cells, available as ATCC Accession No. CCL 61); clones 803 and 677, each of which is a clone of glucuronosyltransferase-deficient CHO K1 cells which lack cell-surface HSPG (in addition, 677 cells overexpress the closely related GAG, chondroitin sulfate); and clone 606, HS-N-sulfotransferase-deficient CHO K1-derived cells which express normal levels of (but under-sulfated) cell surface HSPG. The mutant clones 803, 677, and 606 were obtained from Dr. Jeffrey D. Esko. Wild-type and mutant CHO cells were routinely grown in Hams F12 medium supplemented with 10% bovine fetal calf serum and L-glutamine (Sigma). For transfection of the murine FGF receptor, approximately $4 \times 10^7$ cells were trypsinized, washed in ice cold PBS, and incubated with 50 μg Mo/mFR/SV and 8 μg of CMV B-gal (source; used as a control for transfection efficiency) for 10 min at 4° C. Electroporation was done in a Bio-Rad Gene Pulser at 960uF and 300V. Cells were then plated in 3 cm, 6-well plates, medium was replaced after 24 hours, and b-gal and binding assays were performed 36 to 48 hours after electroporation. Routinely, 30 to 40% of the cells stained positive for b-gal.

Radiolabeling of Recombinant Human bFGF

Recombinant human bFGF was labeled with $^{125}I$ (17 Ci/mg) (New England Nuclear, Boston, Mass.) using Iodo-beads (Pierce Chemical Co., Rockford, Ill.) according to the manufacturer's instructions. Full biological activity of bFGF was retained after iodination, as determined by its ability to stimulate serum-starved Balb/c fibroblasts. When subjected to SDS-PAGE, $^{125}I$-bFGF migrated as a single band in the same position as unlabeled bFGF.

Receptor Binding and Crosslinkin of $^{125}I$-bFGF

Subconfluent cultures of about $2 \times 10^5$ cells in a 30mm dish (Costar) were precooled to 4° C., washed twice with cold Dulbecco's modified Eagle's medium supplemented with 25 mM HEPES pH 7.5 and 1% bovine serum albumin (DMEM/BSA), and incubated for 2 hours at 4° C. with $^{125}$I-bFGF (50 μCi/mmole) in DMEM/BSA at different concentrations and in the presence or absence of heparin, as determined by the experimental protocol. The binding medium was then discarded and the cells washed twice with ice cold PBS and twice with DMEM/BSA. To determine the amount of low-affinity-bound bFGF, the cells were incubated twice for 5 minutes with cold PBS, pH 7.5, containing 1.6M NaCl (low-affinity-bound bFGF could be totally removed using salt concentrations of 0.8M and higher—data not shown), and the radioactivity of the salt extraction solution assayed in a gamma counter. High-affinity-bound bFGF was determined by a 2M NaCl (pH 4.0) extraction (Moscatelli, J. Cell Biol. 107:753-759, 1988). Nonspecific binding was determined by including a 100-fold excess of unlabeled bFGF. After binding in the presence or absence of heparin, bFGF-receptor crosslinking with disuccinimidyl suberate (DSS) was performed as described (Yayon and Klagsbrun, Proc. Natl. Acad. Sci. USA 87:5346-5350, 1990). Briefly, cells were washed twice with PBS and then incubated with 0.15 mM DSS in PBS for 15 minutes at room temperature. The cells were then washed with a solution of 50 mM Tris, pH 7.4, and 100 mM glycine; and scraped and lysed in a small volume of lysis buffer containing 150 mM NaCl, 20 mM Tris pH 8.0, 1 mM MgCl$_2$, 0.1 mM ZnCl$_2$, 0.5% NP-40 (sigma), 1 μg aprotinin (Sigma), 1 μg/ml leupeptin (Sigma), and 2 mM PMSF (phenylmethylsulfonyl fluoride; Sigma). The cell lysate, cleared by spinning down nuclei and cell debris, was boiled and then electrophoresed under reducing conditions on a 7% SDS polyacrylamide gel. After drying the gel, an autoradiogram was prepared using Kodak X-Omat AR film (Eastman Kodak Co., Rochester, N.Y.).

Results

Basic FGF Binds Specifically to Cell Surface Heoaran Sulfate Proteoqlycans

Figure 1A:
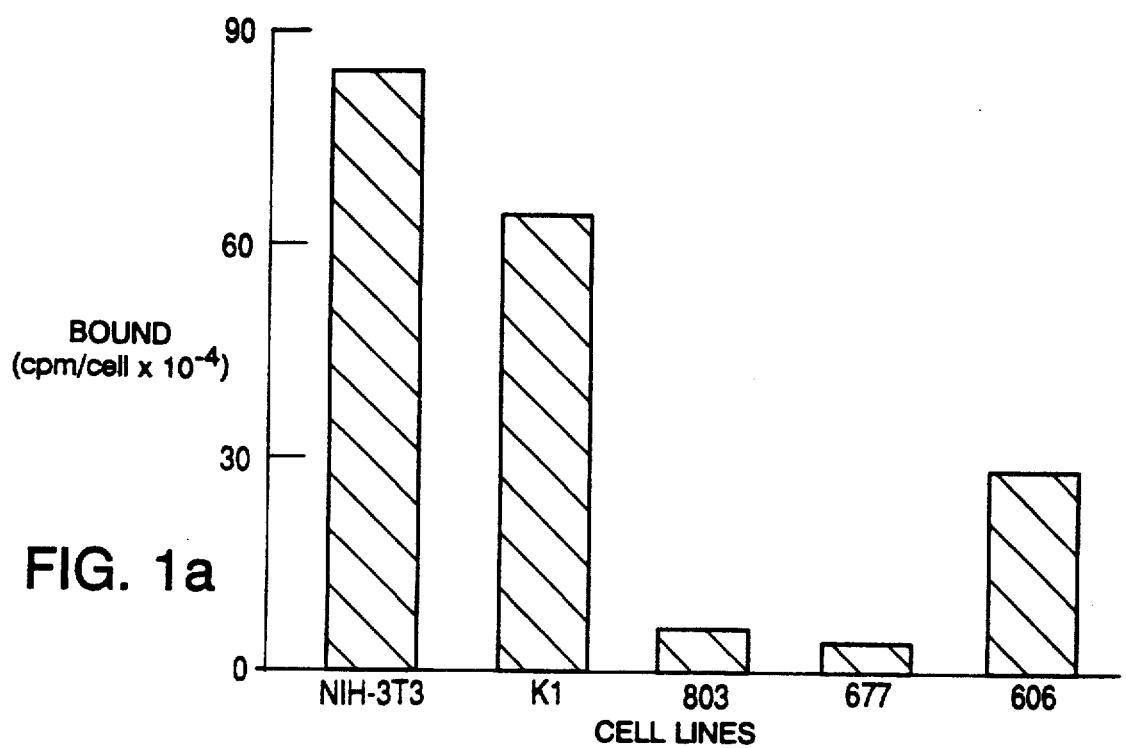
FIG. 1a and FIG. 1b are bar graphs illustrating (FIG. 1a) low affinity and (FIG. 1b) high affinity binding of $^{125}$I-bFGF to wild type NIH-3T3 cells, wild-type CHO K1 cells, cells from clones 803 and 677 (lacking cell-surface HSPG), and cells from clone 606 (having undersulfated cell-surface HSPG).

CHO cell mutants defective at different stages of glycosaminoglycan metabolism (Esko et al., Science 241:1092-1096, 1988), and which also naturally express very low levels of high-affinity FGF receptors (Mansukhani et al., Proc. Natl. Acad. Sci. USA 87:4378-4382, 1990), were used as a model system for analyzing the low-affinity binding sites for bFGF (FIG. 1A). Wild-type CHO cells (K1 cells) were capable of binding bFGF to low-affinity sites in a manner comparable to that found for NIH-3T3 cells. Clone 803 cells (defective in metabolism of heparan sulfate due to glucoronosyl-transferase deficiency and which possess about 5%-10% of the HSPG found in wild-type CHO K1 cells: Esko et al., Science 241:1092-1096, 1988) did not bind significant amounts of bFGF. Absence of low-affinity bFGF binding was similarly observed in experiments using clone 677, which bears the same enzymatic defect and has undetectable levels of HSPG, but which overexpresses the closely related GAG chondroitin sulfate Compared to wild-type CHO cells, low-affinity binding of bFGF was reduced by more than 50% in CHO clone 606, a mutant expressing undersulfated HSPG (Bame and Esko, J. Biol Chem. 264:8059-8065, 1989), confirming a previous report suggesting that the degree of sulfation of heparin can significantly alter its ability to bind aFGF (Sudhalter et al., J. Biol. Chem. 264:6892-6897, 1989). Taken together, these results directly demonstrate that the low-affinity binding sites for bFGF are cell surface and extracellular matrix HSPG.

Cloning the Murine FGF Receptor

Figure 1B:
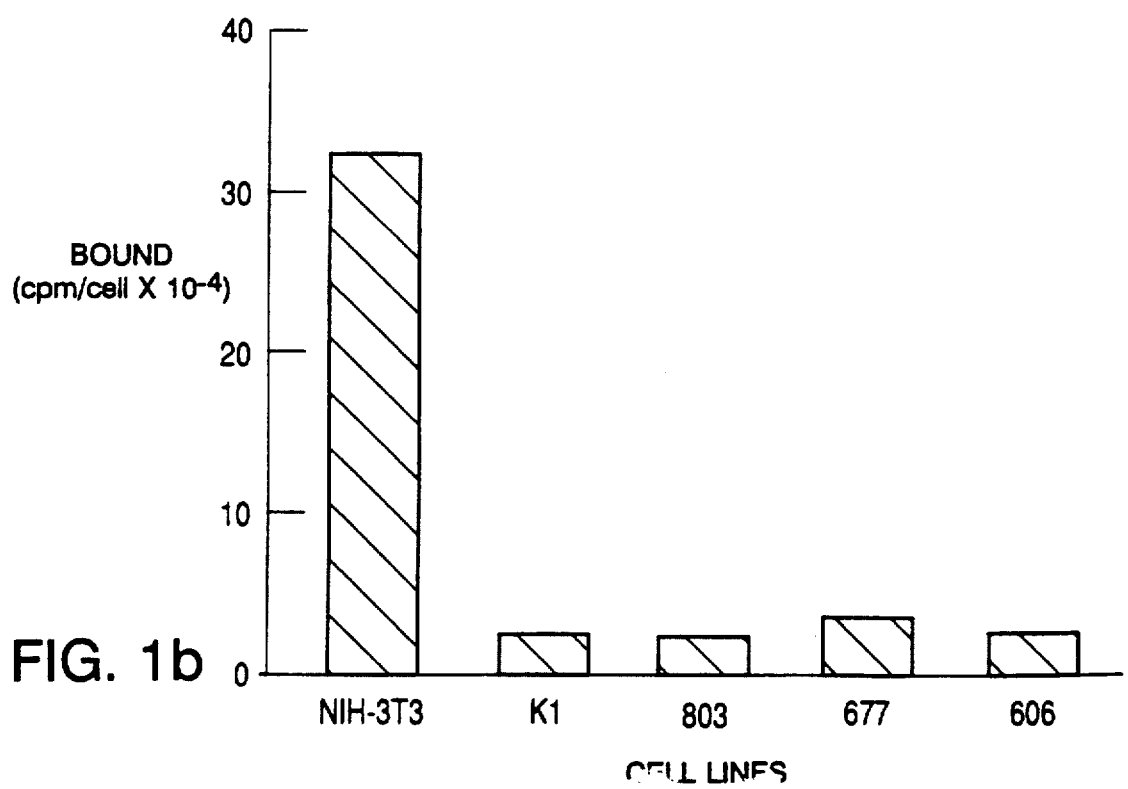

In agreement with a previous report (Mansukhani et al., 1990), wild-type as well as the mutant CHO cells tested express very low levels of high-affinity FGF receptors and exhibited very little high-affinity binding of bFGF when compared to NIH-3T3 cells (FIG. 1B). To investigate the binding properties of the FGF receptor in these HSPG-deficient cells, we cloned a murine homologue of the chicken and human FGF receptors, and constructed a vector to express it efficiently in cultured cells. The strategy used to clone the murine FGF receptor utilized a sequence comparison between chicken (CEK1) and human (hflg) FGF receptor cDNAs and mouse tyrosine kinase cDNA, mBEK. PCR primers designed to match regions highly conserved among these known sequences were used to amplify murine liver cDNA. Comparison of the amplified murine cDNA to CEK1, hFLG, and mBEK revealed that it was more similar to the CEK and flg sequence than to the mBEK sequence (84%, 90%, and 74%, respectively). This amplified murine cDNA, which we have named mFR1, was then used to screen a murine brain cDNA library. Of twelve clones analyzed, one contained a 3.5 kb insert, which when sequenced was found to be highly homologous to both CEK1 and hflg and identical to the recently published murine flg (Reid et al., Proc. Natl. Acad. Sci. USA 87:1596-1600, 1990; Safran et al., Oncogene 5:635-643, 1990).

To express mFR1 in cultured cells, a 3.2 kb fragment containing the entire coding sequence of mFR1 was cloned downstream of the Molony murine leukemia virus long terminal repeat (MoMuLVLTR), and provided with heterologous splice and polyadenylation sequences derived from SV40 (FIG. 2). This plasmid, Mo/mFR1/SV, was transfected into the wild type CHO cell line K1. Binding of $^{125}$I-bFGF was measured after transient transfection of CHO cells with mFR1. The transiently-transfected wild-type CHO cells bound 8-10 fold more $^{125}$I-bFGF than did untransfected cells (FIG. 3A), indicating that the Mo/mFR1/SV plasmid was efficiently expressed and translated to yield a functional FGF receptor.

Figure 4:
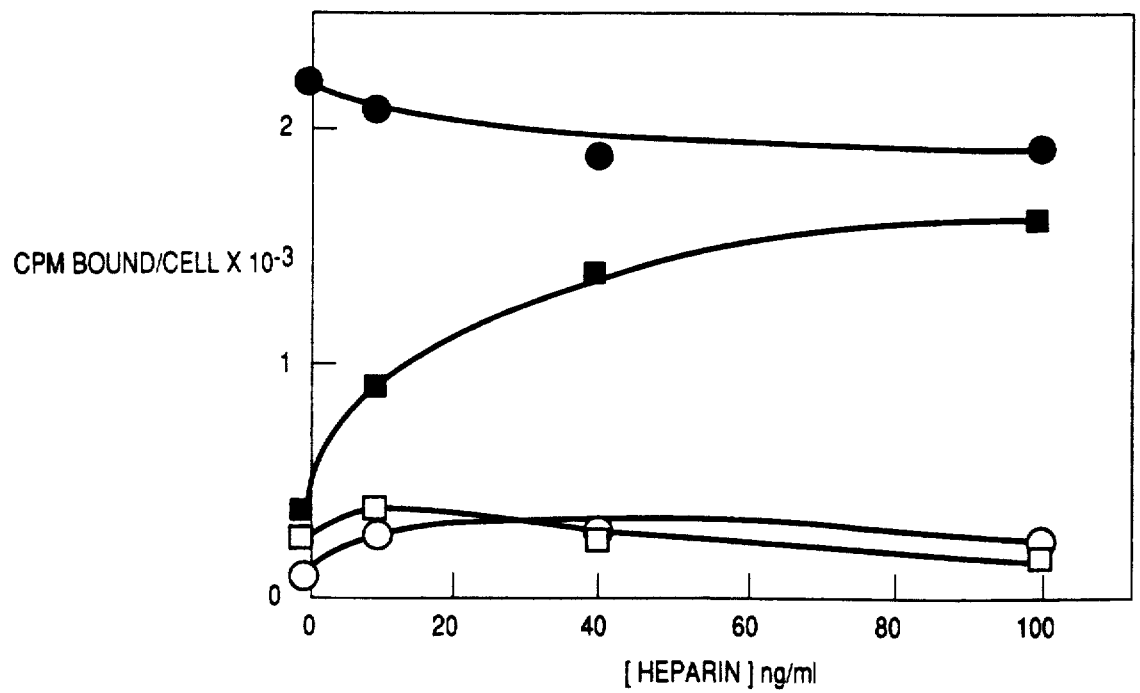
FIG. 4 is a graph illustrating the effect of heparin concentration on bFGF binding in CHO K1 cells (circles) and 803 cells (squares), expressing (closed symbols) and not expressing (open symbols) mFR1.
Figure 3A:
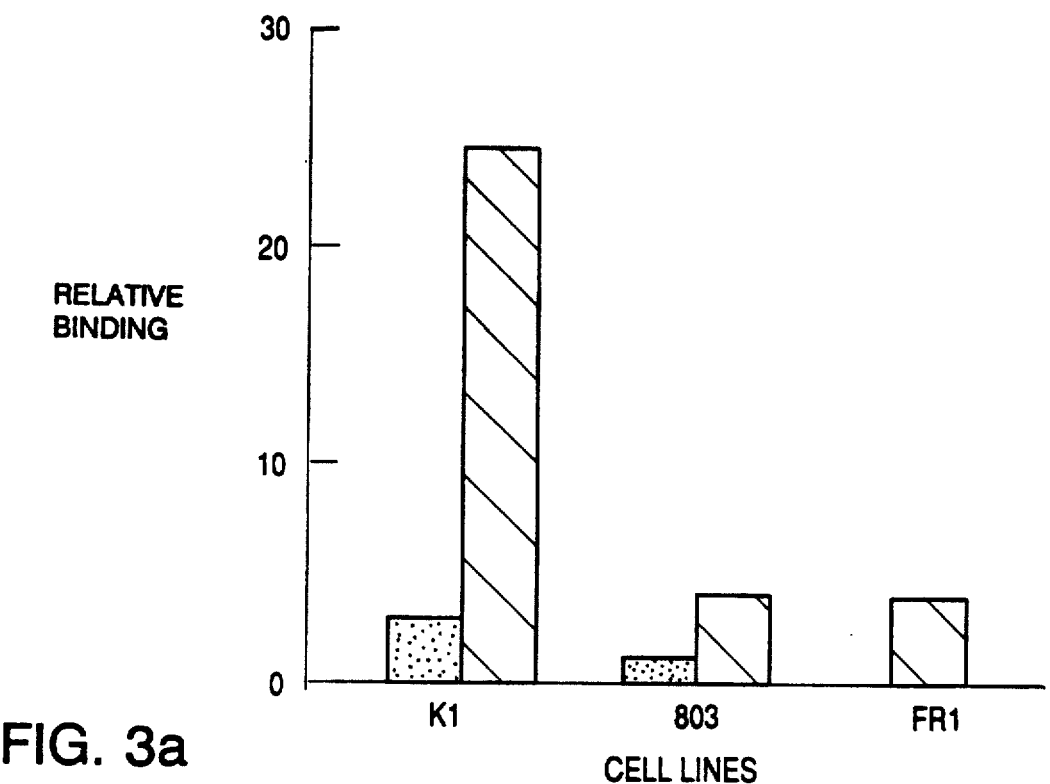
FIG. 3a and FIG. 3b are bar graphs illustrating relative degrees of high-affinity receptor binding of $^{125}$I-bFGF in the absence (FIG. 3a) or in the presence (FIG. 3b) of 40 ng/ml heparin, determined before (strippled bars) or 48 hours after (crosshatched bars) transient transfection of MFR1 into CHO K1 and 803 cells; also shown is the relative binding of 803-FR1 cells, a clone of 803 cells stably transfected with mFR1.
Figure 3B:
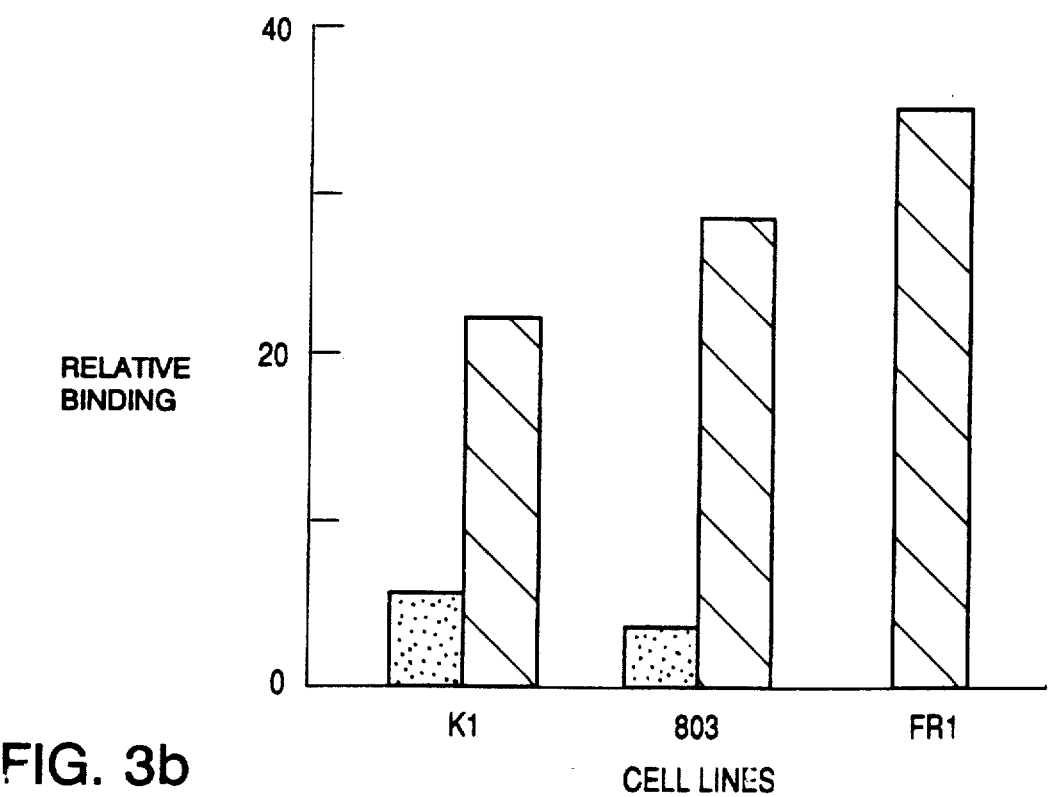

CHO Mutants Transfected With High-affinity FGF-receptor as a Model for Studying High- and Low-affinity Receptor Interactions Wild type CHO K1 cells transfected with the Mo/mFR/SV plasmid demonstrated high levels of high-affinity binding of bFGF (FIG. 3A). However, none of the similarly transfected HS-deficient mutants showed significant high-affinity binding of bFGF. High-affinity receptor binding of bFGF in these mFR1-transfected, HS-deficient mutants could be fully restored by inclusion of heparin in the binding medium (FIG. 3B). Heparin-dependent receptor binding was demonstrated independently in two HS-deficient, transiently transfected clones (clones 803 and 677) and in an isolated, stably expressing, HS-deficient clone (clone 803-FR1). These results suggest that cell surface low-affinity-binding HSPGs are needed to promote high-affinity bFGF binding, but that soluble heparin can substitute Shown in FIG. 4A is a dose-response curve illustrating the effect of varying concentrations of heparin on binding of bFGF to its high-affinity receptor. These results demonstrate a saturable binding curve with maximal receptor binding at heparin concentrations as low as 40 ng/ml, suggesting a highly specific bFGF-heparin interaction. As expected, there was no detectable potentiating effect of heparin on the high-affinity binding of bFGF mFR1-transfected wild type CHO K1 cells, which express ample cell surface HSPG. These cells register high levels of bFGF binding both in the presence and in the absence of heparin, suggesting that exogenously-applied heparin and cell surface HS or heparin-like molecules can interchangeably function as accessory molecules to promote binding of bFGF to the high-affinity FGF receptor.

Figure 5A:
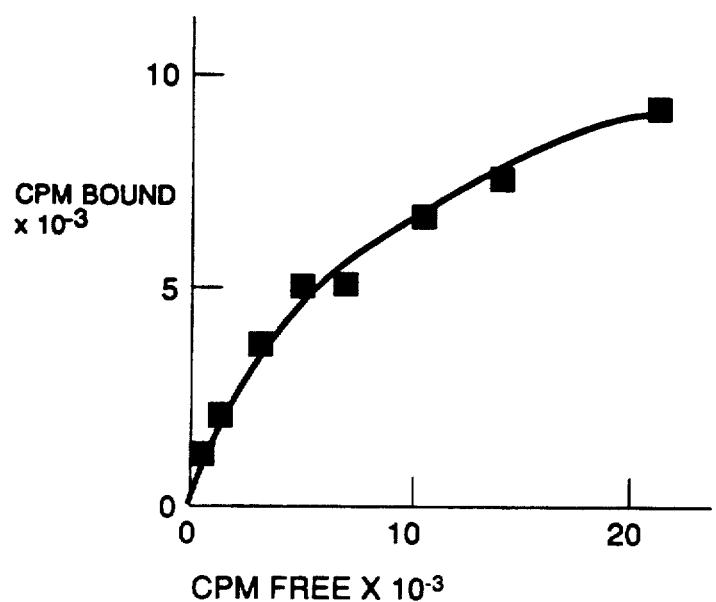
FIG. 5a is a graph showing bound $^{125}$I-bFGF as a function of concentration of free bFGF in the presence of 40 ng/ml heparin, using HS-deficient cells expressing FGF receptors.
Figure 5B:
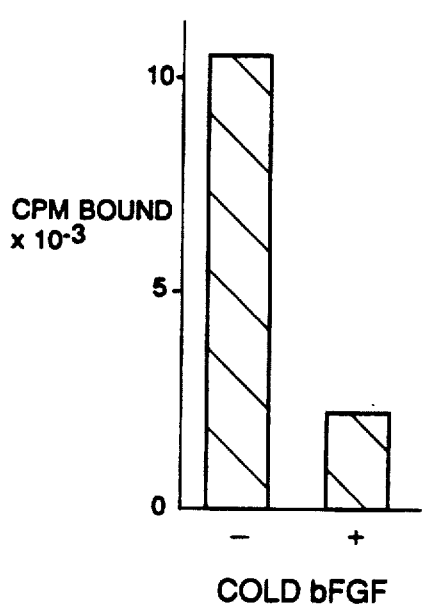
FIG. 5b is a bar graph showing binding of $^{125}$I-bFGF to HS-deficient cells expressing FGF receptors, in the presence (+) or absence(−) of excess unlabelled bFGF.
Figure 5C:
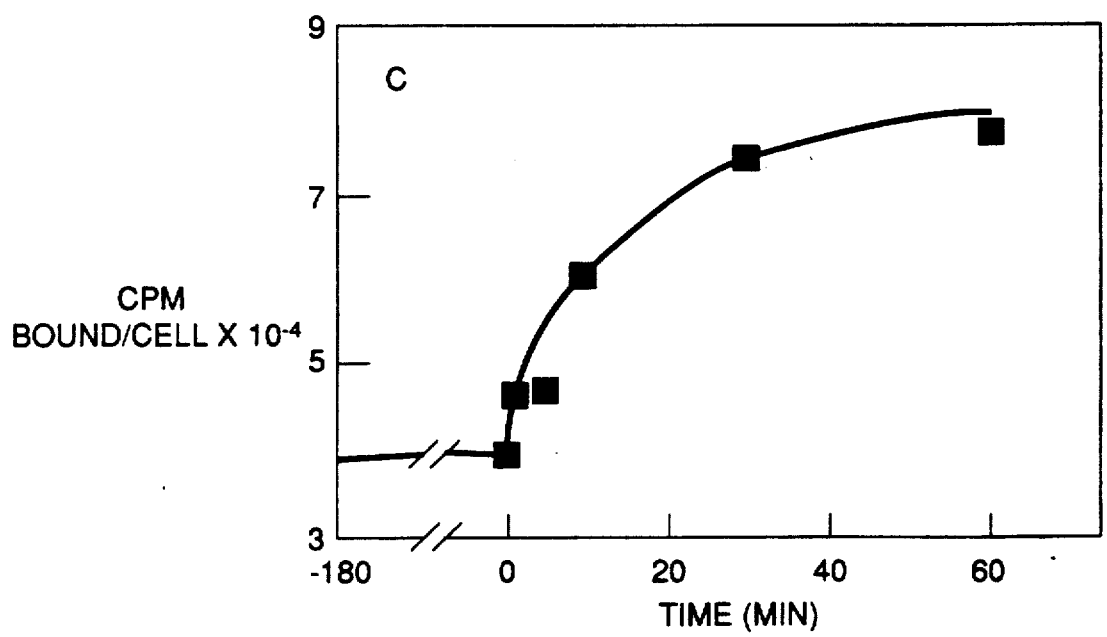
FIG. 5c is a graph showing the time course for high-affinity binding of $^{125}$I-bFGF to HS-deficient, FGF receptor-expressing cells, with 1 μg/ml heparin added at time zero.

Basic FGF-receptor binding to HS-deficient cells in the presence of 40 ng/ml heparin revealed a specific, saturable, single class of high-affinity binding sites (FIG. 5A). The heparin-dependent high-affinity receptor binding was similar to that reported for non-heparin-dependent binding of bFGF to cells which naturally express both HSPG and high-affinity receptors for bFGF (Neufeld et al., J. Biol. Chem. 261:5631–5637, 1985). Similarly, heparin-dependent, high-affinity receptor binding was specifically competed out by an excess of unlabeled bFGF (FIG. 5B). A kinetic study of the effect of heparin on high-affinity bFGF binding to HS-deficient cells revealed a very rapid response to exogenously-added heparin, with a half-maximal response time at 4° C. of less than 10 minutes (FIG. 5C). Such a rapid response strongly suggests that binding of bFGF to heparin or cell surface HSPG is a rate-limiting step in the binding of bFGF to its high-affinity receptor. In addition, this result implies that the ability to restore high-affinity receptor binding by heparin is not due merely to stabilization of bFGF by heparin (Gospodarowicz and Chen, J. Cell Physiol 128:475–484, 1986; Saskela et al., J. Cell. Biol. 107:743–751, 1988) a high-affinity bFGF binding could be rapidly and fully restored even after a 3 hour preincubation in the absence of heparin. Moreover, aliquots of the binding medium, taken at the end of each experiment with or without heparin, showed no signs of degradation of bFGF, as evidenced by gel electrophoresis and a biological activity assay (not shown). Taken together, these results suggest that the ability of heparin to promote high-affinity receptor binding is not due to its stabilizing effect, but rather to its ability to confer upon bFGF an active, receptor-compatible conformation.

The Ability to Reconstitute High-affinity Binding is Specific to Heparin

The specificity of heparin in promoting high-affinity receptor binding was demonstrated by comparing the effect of heparin to that of each of the following: the closely related glycosaminoglycan chondroitin sulfate; an undersulfated kidney-derived HS; a highly-sulfated lung-derived HS; and a small, chemically-defined, twelve-sugar heparin fragment While both chondroitin sulfate and the undersulfated HS did not promote high-affinity receptor binding, the sulfated HS was as active as heparin and the twelve-sugar heparin fragment was 70% as active as full-length heparin (FIG. 6A). Moreover, pretreatment of active heparin preparations with heparinase, a specific heparin-degrading enzyme, completely abolished their capacity to restore high-affinity receptor binding (FIG. 6B), suggesting that heparin is indeed the active fraction in these preparations.

Chemical Crosslinking of $^{125}$I-bFGF to Wild-type and HS-deficient CHO Cells

Figure 7:
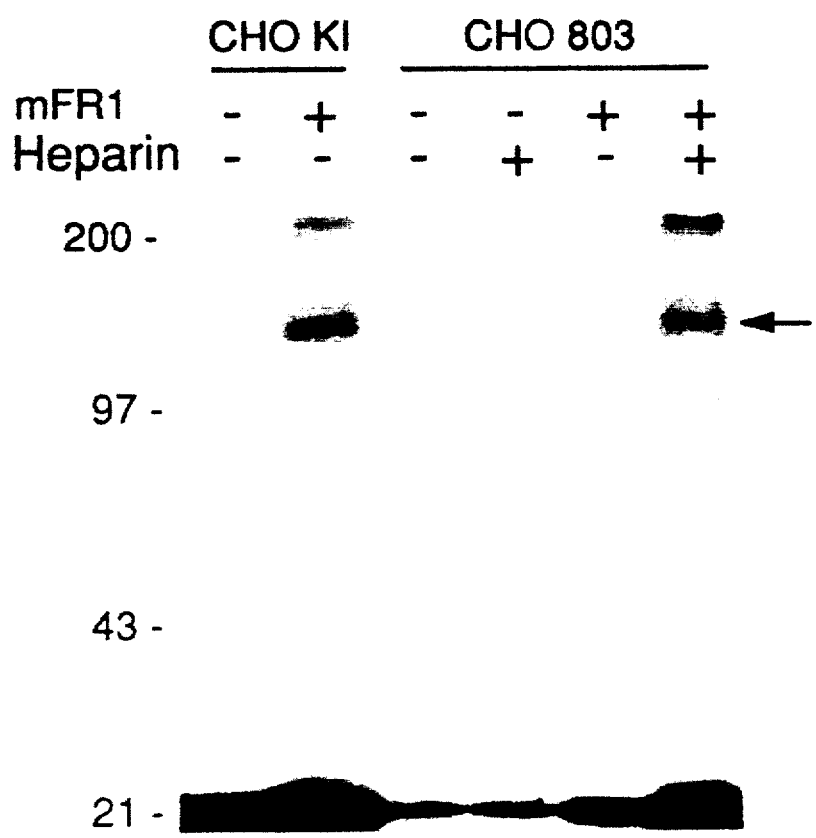
FIG. 7 is a copy of an autoradiogram illustrating the size, as assayed by PAGE, of the species labelled by crosslinking $^{125}$I-bFGF to wild-type (CHO K1) and mutant (CHO 803) cells transiently transfected with Mo/mFR1/SV, in the presence (+) or absence (−) of 40 ng/ml heparin.
Figure 8:
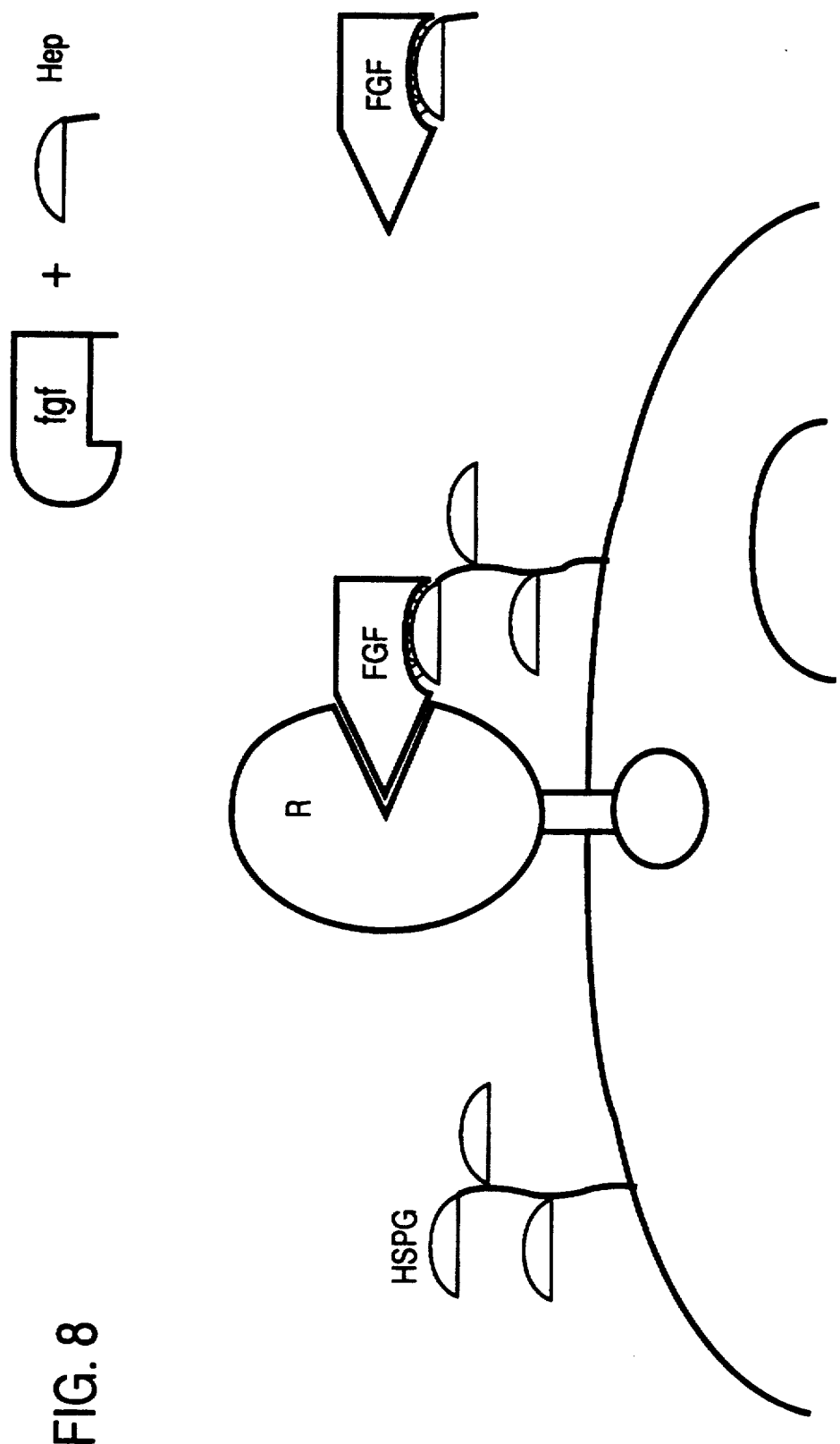
FIG. 8 is a schematic diagram illustrating a proposed "induced fit" model for heparin-dependent high-affinity-receptor binding of FGF, wherein heparin or cell-surface HSPG induces a conformational change in the FGF molecule, enabling it to bind to the high-affinity receptor (R).

Crosslinking of $^{125}$I-bFGF to wild-type CHO cells transfected with the mouse FGF receptor cDNA demonstrated a bFGF-receptor protein complex with an apparent molecular weight of 150 kD (FIG. 7), identical in size to that observed when $^{125}$I-bFGF is crosslinked to receptors on NIH-3T3 fibroblasts, which naturally express the FGF receptor (Yayon and Klagsbrun, Proc. Natl. Acad. Sci. USA 87:5346–5350, 1990). In contrast, bFGF could not be crosslinked to high-affinity receptors expressed on HS-deficient cells unless heparin was included in the binding medium prior to crosslinking. These results are in agreement with the radioreceptor binding data shown in FIG. 3, and provide further evidence for the failure of bFGF to bind to high-affinity receptors expressed in HS-deficient cells, confirming our observation that heparin or a heparin-like molecule is an absolute requirement for high-affinity receptor binding of bFGF.

EXAMPLE 2: CELL-FREE SYSTEM

Experimental Procedures

Recombinant Fusion Gene Construction

The mouse bFGF receptor/alkaline phosphatase fusion gene ("FRAP") was constructed by inserting a DNA sequence encoding a portion of the mouse bFGF receptor gene product into plasmid APtag-1, which encodes a secreted form of placental alkaline phosphatase (SEAP). The APtag-1 vector was constructed as described in Leder et al., U.S. Ser. No. 07/593,764, herein incorporated by reference In APtag-1, the first codon of the mature SEAP protein (Berger et al., Proc. Natl. Acad. Sci. USA 84:4885, 1987, hereby incorporated by reference; Berger et al., Gene 66:1, 1988, hereby incorporated by reference) is immediately preceded by the nucleotide sequence (SEQ 1D NO: 2):

| KpnI | HindIII | SnaBI | BglII | BspMII |
|------|---------|-------|-------|--------|
| GG TAC | CAA GCT | TAC GTA | AGA TCT | TCC GGA |

This sequence includes cloning sites into which genes or gene fragments may be inserted to produce an APtag fusion protein. The structure of APtag-1 allows for the production of a fusion protein with an enzyme tag at its C-terminal end. The KpnI site shown above marks the 3' end of a 625 bp ClaI to KpnI fragment of the Moloney murine leukemia virus LTR; this fragment is flanked on its 5' side by sites for SnaBI, EcoRI, SalI and ClaI. The remainder of APtag-1 is the same as nucleotides 62 to 5212 of pBC12/PL/SEAP. Thus the relevant portion of APtag-1 includes, in the following order: restriction enzyme sites SnaBI, EcoRI, SalI, and ClaI; a 625 bp ClaI-KpnI fragment of the Moloney mouse leukemia virus LTR (Genebank Accession Nos. J02255, J02256, J02257); the restriction enzyme sites KpnI, HindIII, SnaBI, BolII, and BsoMII; and nucleotides 62 to 5212 of plasmid pBC12/PLAP (Berger et al., Gene 66:1, 1988), including a sequence encoding amino acids 1 to 489 of secreted placental alkaline phosphatase, a 3'-intronic region and the polyadenylation site of the rat preproinsulin II gene (Lomedico et al., Cell 18:545, 1979, hereby incorporated by reference), the SV40 origin of replication, and the entire sequence of pXF3, a poison sequence-minus derivative of pBR322 (Hanahan et al., *J. Mol. Biol.* 166:557, 1983, hereby incorporated by reference; Cullen et al., *Cell* 46:973, 1986, hereby incorporated by reference). The Ig heavy chain promoter and enhancer, the CMV enhancer, or the Rous sarcoma virus LTR may, for example, be used in place of the Moloney murine leukemia virus LTR to direct expression of the hybrid protein; and an SV40 intron and splice site may, for example, be used in place of the rat preproinsulin sequence.

Figure 11A:
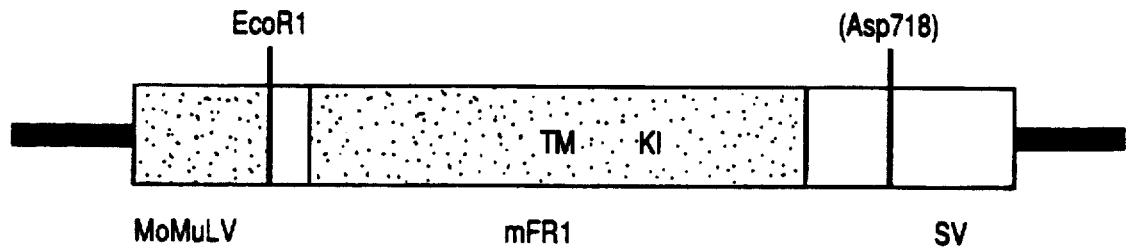
FIG. 11a is a schematic diagram of the mFR1 plasmid.
Figure 11B:
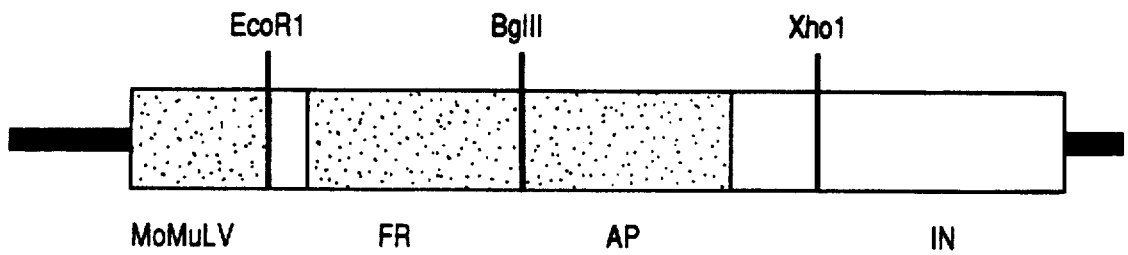
FIG. 11b is a schematic diagram of the FRAP plasmid.

SEAP was chosen as the enzyme tag for a number of reasons, including the availability of a variety of indicator substrates for alkaline phosphatases, the high specific activity of the mammalian enzymes, the high stability, including stability to heat, of the placental isozyme, and the availability of isozyme-specific inhibitors that can be used to reduce background phosphatase activities (Berger et al., *Gene* 66:1, 1988; Harlow and Lane, *Antibodies: a laboratory manual,* Cold Spring Harbor Laboratory, Cold Spring Harbor, N.Y., 1988, hereby incorporated by reference; Zoellner and Hunter, *J. Histochem. Cytochem.* 37:1893, 1989, hereby incorporated by reference). In addition, proteolytic digestion studies have indicated that both the N- and C-termini of the protein are dispensable for activity (Jemmerson et al. in *Human Alkaline Phosphatases,* T. Stigbrand & W. H. Fishman, Liss, N.Y., 1983, hereby incorporated by reference), making it likely that protein fusions at either end would leave the enzyme activity intact To generate a FGF receptor/SEAP fusion protein, the 5' end of a mouse bFGF receptor cDNA sequence, including sequences encoding the FGF secretion signal peptide and the entire extracellular domain (i.e., ending at amino acid 374, immediately before the first hydrophobic amino acid of the transmembrane region), was inserted into APtag-1. The Mo/mFR1/SV plasmid described in the related Yayon et al. patent application was cut with ClaI and HincII to produce a DNA fragment containing the Molony virus LTR and most of the sequence of mFR1 5' of the transmembrane domain, up to the HincII restriction site at nucleotide 1342. This fragment was incorporated into ClaI/BglII-digested APtag in a three-way ligation using as a linker a PCR fragment which includes a sequence encoding (a) the remainder of mFR1 adjacent to the transmembrane domain, and (b) a BglIII restriction site. This PCR fragment was generated from the mFR1 template, using a 5' primer (GGAGATCTCCCATCACTCT-GCATGGTTG) (SEQ ID NO: 3) which corresponds to nucleotides 1317-1343 of the mFR1 sequence (just 5' to the HincII site), and a 3' primer (CGGAA-GATCTCTCCAGGTAGAGCG) (SEQ ID NO: 4) corresponding to nucleotides 1390-1404 of the mFR1 sequence plus (at its 5' end) a BglII restriction site. The three-way ligation resulted in a plasmid having the structure diagrammed in FIGS. 10 and 11. Sequencing confirmed the open reading frame at the two ligation points flanking the PCR fragment.

Expression of the FRAP Fusion Protein

The FRAP fusion protein was produced in a mammalian cell line stably transfected with the FRAP plasmid, as follows: the FRAP plasmid was linearized with ClaI and was co-transfected, along with the selectable marker plasmid CMVNeo (described in Schmidt et al., Mol. Cell Biol. 10:4406-4411, 1990, hereby incorporated by reference), into NIH 3T3 cells using the electroporation technique described in Potter et al., *Proc. Natl. Acad. Sci.* 81:7161, 1984, hereby incorporated by reference. Cells were then grown in DMEM (Sigma) containing 10% bovine calf serum (Hyclone Laboratories Inc., Logan, Utah), and after selection with 400 µg/ml G418 (Life Technologies Inc., Grand Island, N.Y.), approximately 100 neo$^R$ clones were screened for secretion of placental alkaline phosphatase activity. The alkaline phosphatase assay was performed by heating a portion of the supernatant at 65° C. for 10 min to inactivate background phosphatase activity, and then measuring the OD$_{405}$ following incubation in a solution of 1M diethanolamine, pH 9.8 (Sigma); 0.5 mM MgCl$_2$; 10 mM L-homoarginine (a phosphatase inhibitor; Sigma) 0.5 mg/ml BSA (Sigma cat. no. A-7638); and 12 mM p-nitrophenyl phosphate (Sigma cat. no. 104–105), prepared as a single 2X stock solution. The highest AP-expressing clone, termed FRAP-A2, was used for production of the FRAP fusion protein. Further characterization of the FRAP-A2 fusion polypeptide is accomplished in accordance with the methods described in Leder et al., U.S. Ser. No. 07/593,764.

Assay for FGF-binding Activity

Figure 12:
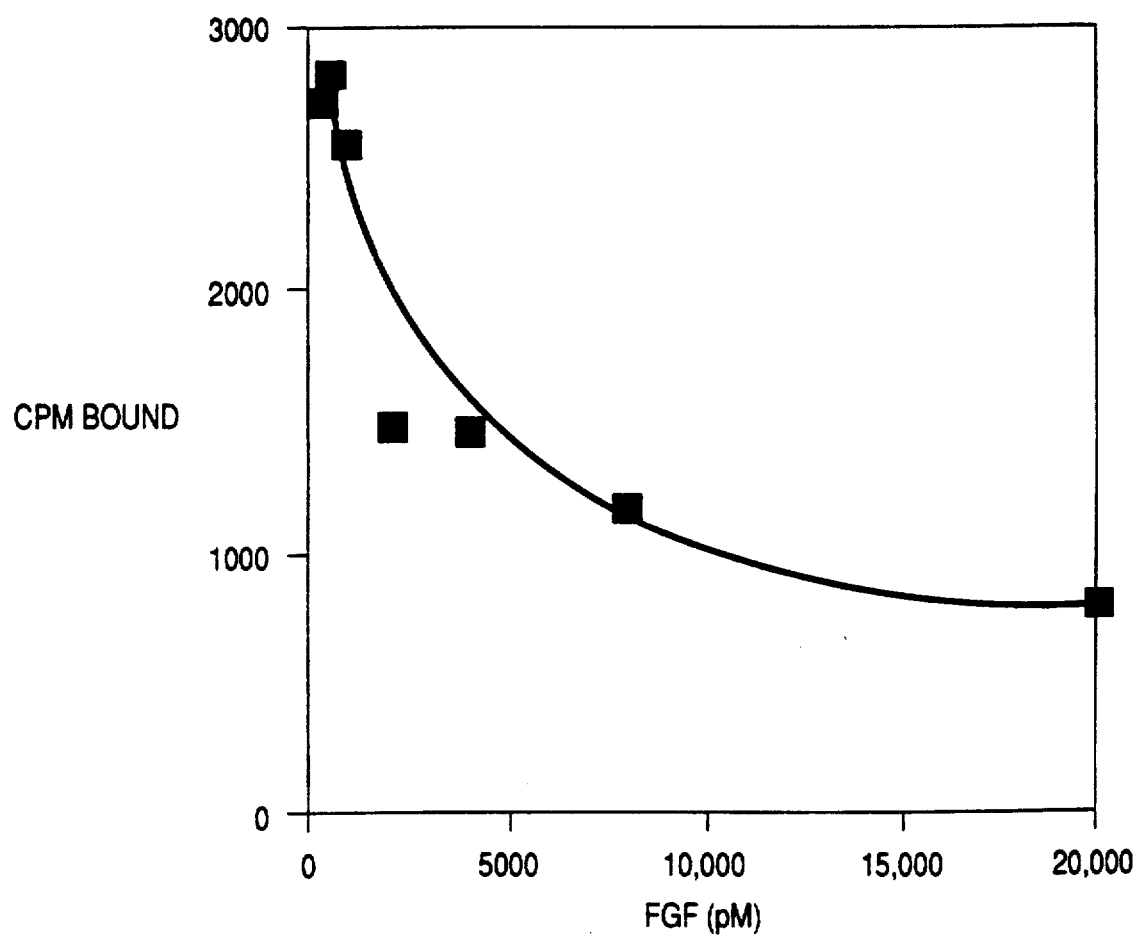
FIG. 12 is a graph illustrating a competition assay, the amount of $^{125}$I-bFGF bound to FRAP in the presence of increasing amounts of unlabelled bFGF was measured.
Figure 13:
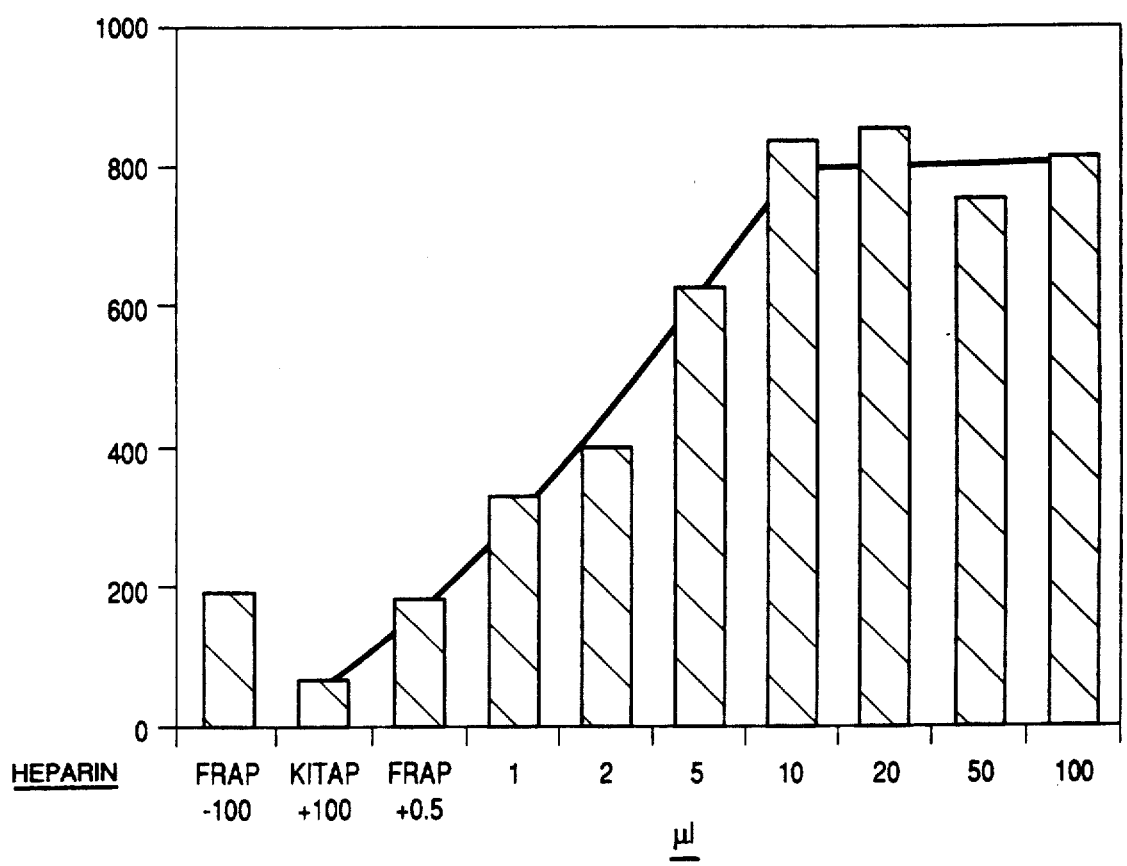
FIG. 13 is a bar graph illustrating that as the amount of FRAP protein present in the assay sample increases (indicated as ul of conditioned medium derived from cells transfected with and expressing the FRAP plasmid), the amount of $^{125}$I-bFGF bound to and immunoprecipitated by the AP-specific monoclonal antibody increases.
Figure 14:
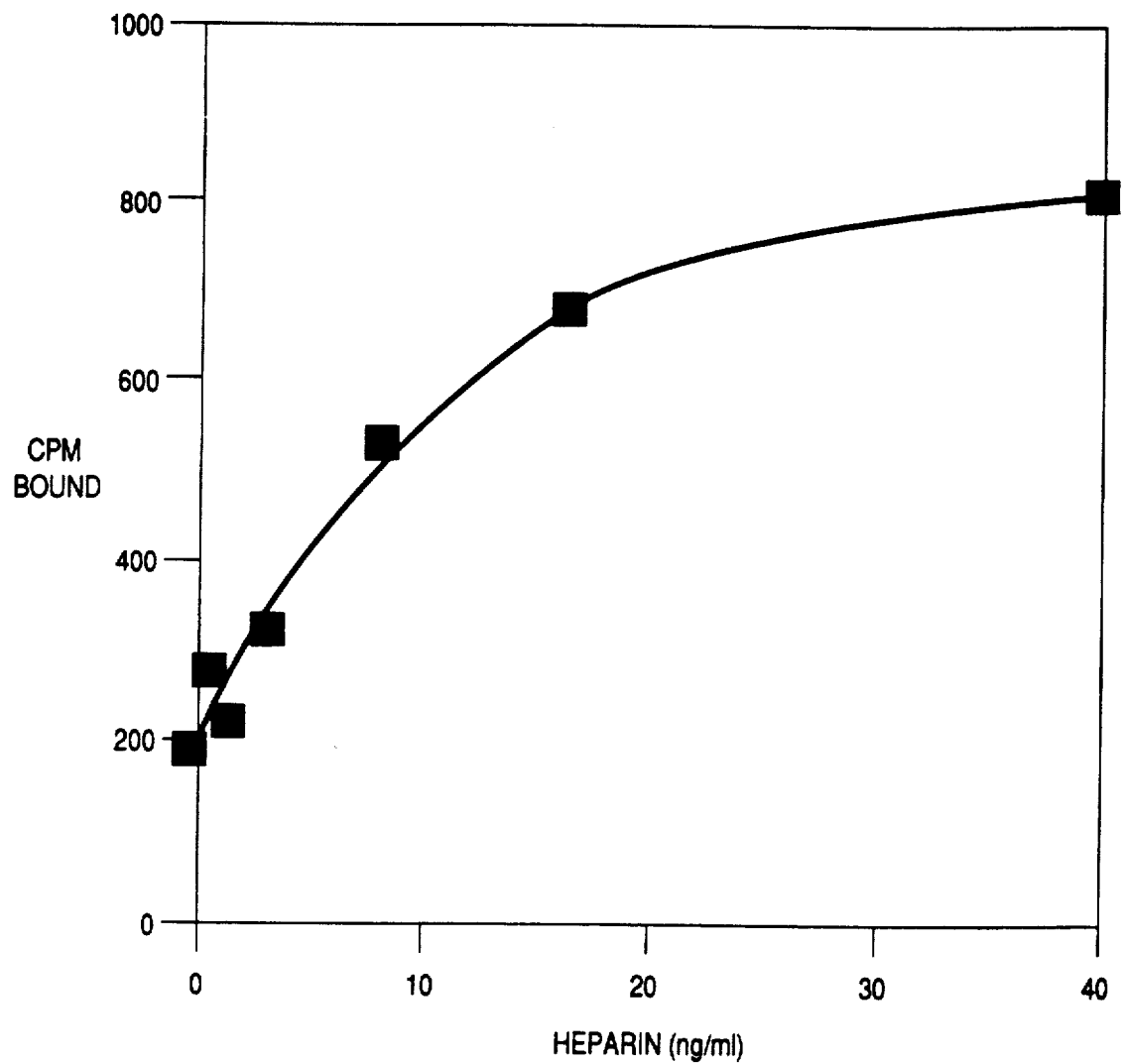
FIG. 14 is a graph showing the dependence on heparin concentration of binding of $^{125}$I-bFGF to FRAP protein (as immunoprecipitated by the AP-specific monoclonal antibody)

Conditioned medium from FRAP-A2 was assayed for its ability to bind $^{125}$I-bFGF by combining in the presence or in the absence of a standard amount of heparin, an aliquot of conditioned medium with a standard amount of $^{125}$I-bFGF and a standard amount of monoclonal antibody specific for placental alkaline phosphatase (Medix Biotech, Foster City, Calif.) coupled to CNBr-activated sepharose beads (Pharmacia, Piscataway, N.J.). The mixture was incubated for 90 min at 4° C. and centrifuged to pellet the beads, which were then washed two times with 0.5 ml PBS and repelleted before FIG. 12 shows the results of a competition assay in which bound $^{125}$I was found to decrease with increasing concentrations of unlabelled FGF. In the experiment illustrated in FIG. 13, varying amounts of FRAP-A2-conditioned medium were combined with heparin and $^{125}$I-bFGF, while in FIG. 14 the variable was the concentration of heparin in the assay mix.

Other embodiments of the invention are within the following claims.

---

What is claimed is:

1. A homogeneous in vitro population of mammalian cells having on average a number of cell surface low-affinity HBGF-binding sites per cell less than 20% of the number of such binding sites found on wild-type CHO-K1 cells (ATCC Accession No. CCL61), and on average at least three times the number of cell surface high-affinity HBGF receptors per cell found on said CHO-K1 cells.

2. The population of cells of claim 1 wherein each of the cells in said population comprises a recombinant nucleic acid encoding said high-affinity HBGF receptor.

3. The population of cells of claim 1, wherein said high-affinity HBGF receptor is endogenous to a species selected from the group consisting of human, mouse, and chicken.

4. The population of cells of claim 3, wherein said high-affinity HBGF receptor is a mouse high-affinity HBGF receptor.

5. The population of cells of claim 1, wherein said high-affinity HBGF receptor is a high-affinity aFGF or bFGF receptor.

6. The population of cells of claim 2, wherein said recombinant nucleic acid is incorporated into the genome of each cell of said population.

7. The population of cells of claim 2, wherein each cell of said population is transiently transfected with a vector comprising said recombinant nucleic acid.

8. A system for assaying the ability of a substance to bind to a high-affinity HBGF receptor, which system comprises a cell of the population of cells of claim 1 (the "test cell"), and an amount of heparin or a heparin-like molecule sufficient to induce binding of a HBGF to a high-affinity HBGF receptor on said test cell.

9. A system for assaying the ability of a substance to affect the interaction between a given type of HBGF and a high-affinity HBGF receptor, which system comprises said given type of HBGF and a cell of the population of cells of claim 1.

* * * * *

UNITED STATES PATENT AND TRADEMARK OFFICE
CERTIFICATE OF CORRECTION

PATENT NO. : 5,270,197  
DATED : December 14, 1993  
INVENTOR(S) : Avner Yayon, et al Page 1 of 3

Figure 6:
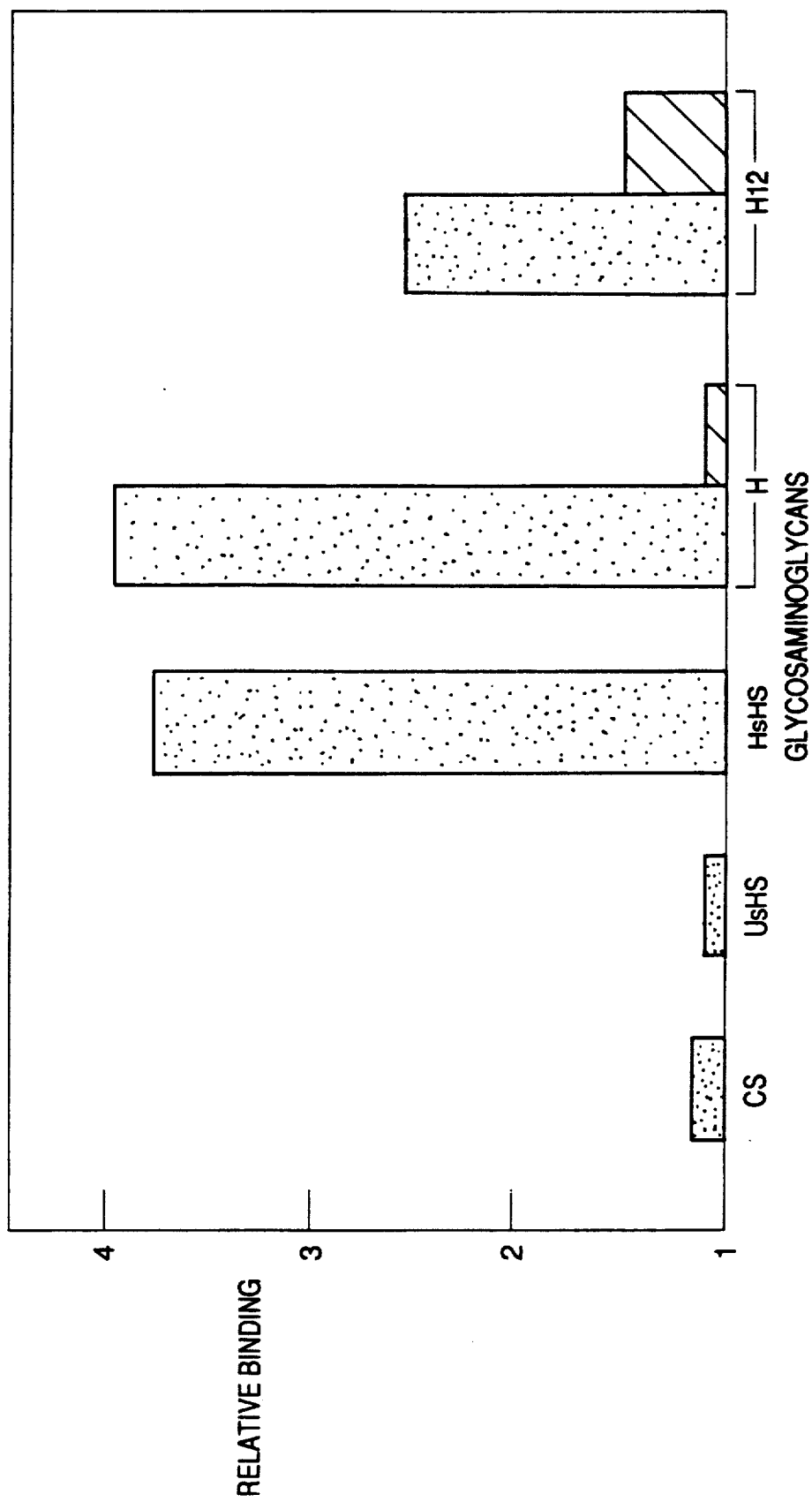
FIG. 6 is bar graph illustrating relative $^{125}$I-bFGF to 803-FR1 cells in the absence or presence of chondroitin sulfate ("CS"); under-sulfated, kidney-derived HS ("UsHS"); highly-sulfated lung-derived HS ("HsHS"); heparin ("H"); or a 12-sugar heparin fragment ("H12"); or after incubation of heparin or the heparin fragment with heparinase prior to the binding assay (hatched bars).

It is certified that error appears in the above-indentified patent and that said Letters Patent is hereby corrected as shown below:

Column 1, line 22, replace "lease" with --least--;

Column 3, line 16, replace "proteins thus, a cell of" with --proteins: thus, a cell of --;

Column 4, line 54, replace "receptor binding of" with --receptor binding by --;

Column 5, line 9, replace "FIG. 6 is bar graph" with --FIG. 6 is a bar graph--; same line, add "binding" after "$^{125}$I-bFGF";

Column 5, line 41, add "wherein" before "the amount of";

Column 5, line 54, add a period at the end of the line;

Column 6, line 1, replace "auqments" with --augments--;

Column 7, line 51, replace "(SEQ ID NO: 3)" with --(SEQ ID NO : 5);

Column 9, line 39, in the heading, replace "Heoaran" with --Heparan--;

Column 9, line 40, in the heading, replace "Proteoqlycans" with --Proteoglycans--.

UNITED STATES PATENT AND TRADEMARK OFFICE
CERTIFICATE OF CORRECTION

PATENT NO. : 5,270,197
DATED : December 14, 1993
INVENTOR(S) : Avner Yayon, et al It is certified that error appears in the above-indentified patent and that said Letters Patent is hereby corrected as shown below:

Column 10, line 68, add a period after "substitute";

Column 11, line 40, replace "a" with --as--;

Column 12, lines 62, replace "BolII" with --BglII--; same line, replace "BsoMII" with --BspMII--;

Column 13, line 47, replace "BglIII" with --BglII--;

Column 14, line 48, after "before", add the following: --determining the amount of bound $^{125}$I in a gamma counter.--;

Column 21, replace "(2) INFORMATION FOR SEQ ID NO: 2" with --(3) INFORMATION FOR SEQ ID NO: 2--;

Column 21, replace "(2) INFORMATION FOR SEQ ID NO: 3" with --(4) INFORMATION FOR SEQ ID NO: 3--;

UNITED STATES PATENT AND TRADEMARK OFFICE
CERTIFICATE OF CORRECTION

PATENT NO. : 5,270,197
DATED : December 14, 1993
INVENTOR(S) : Avner Yayon, et al It is certified that error appears in the above-indentified patent and that said Letters Patent is hereby corrected as shown below:

Column 21, replace "(2) INFORMATION FOR SEQ ID NO: 4" with --(5) INFORMATION FOR SEQ ID NO: 4--;

Column 21, replace "(2) INFORMATION FOR SEQ ID NO: 5" with --(6) INFORMATION FOR SEQ ID NO: 5--.

Signed and Sealed this

Fourteenth Day of June, 1994

Attest:

BRUCE LEHMAN

*Attesting Officer*    *Commissioner of Patents and Trademarks*